(12) United States Patent
Fleming et al.

(10) Patent No.: US 9,481,645 B2
(45) Date of Patent: Nov. 1, 2016

(54) COMPOSITION, SYNTHESIS, AND USE OF A NEW CLASS OF ISONITRILES

(71) Applicant: DUQUESNE UNIVERSITY OF THE HOLY GHOST, Pittsburgh, PA (US)

(72) Inventors: Fraser Fergusson Fleming, Falls Church, VA (US); Jesus Armando Lujan-Montelongo, Tlalnepantla de Baz (MX)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 0 days.

(21) Appl. No.: 14/627,360

(22) Filed: Feb. 20, 2015

(65) Prior Publication Data

US 2015/0239835 A1    Aug. 27, 2015

Related U.S. Application Data

(60) Provisional application No. 61/942,843, filed on Feb. 21, 2014.

(51) Int. Cl.
*C07C 323/25* (2006.01)
*C07C 323/26* (2006.01)
*C07C 249/02* (2006.01)

(52) U.S. Cl.
CPC .......... *C07C 323/26* (2013.01); *C07C 249/02* (2013.01); *C07C 323/25* (2013.01); *C07C 2101/08* (2013.01); *C07C 2101/14* (2013.01)

(58) Field of Classification Search
None
See application file for complete search history.

(56) References Cited

U.S. PATENT DOCUMENTS

| 4,584,012 | A   | * | 4/1986 | Singh .................... A01N 25/32 504/108 |
|---|---|---|---|---|
| 8,269,032 | B1 |   | 9/2012 | Fleming et al. |
| 8,563,763 | B2 |   | 10/2013 | Fleming et al. |
| 2009/0264425 | A1 |   | 10/2009 | Jones et al. |
| 2012/0259137 | A1 |   | 10/2012 | Fleming et al. |

FOREIGN PATENT DOCUMENTS

CS        0213038 B1 * 3/1989
WO    WO 2010136940 A1 * 12/2010 .............. C07J 3/005

OTHER PUBLICATIONS

Cervena et al., Collect. Czech. Chem. Commun. (1981), 46, 1188-1198.*
Sindelar et al. Collection of Czechoslovak Chemical Comm. (1982), 47(5), 1367-81.*
Sulfinyl-Metal Exchange-Alkylation Strategies, Nath et al. Chemistry Eur. J. (2013), 19, 2023-2029, 2025 (published Online Dec. 23, 2012).*
PubChem; "Compound Summary for CID 2759896"; PubChem; 40929-75-7 | C9H13NO2; Jul. 9, 2005; pp. 1-10.
PubChem; "Compound Summary for CID 57917879"; PubChem; AGN-PC-0C2W8X |C14H9C12NOS; Aug. 19, 2012; pp. 1-11.

* cited by examiner

*Primary Examiner* — Nyeemah A Grazier
(74) *Attorney, Agent, or Firm* — Eckert Seamans Cherin & Mellott, LLC; Carol A. Marmo

(57) ABSTRACT

This invention relates to novel isonitriles, including arylthio isonitriles, and methods for their preparation. The isonitriles include a conjugated ring system. The structure is designed with the flexibility to have multiple substitution patterns. The isonitriles may be used in applications including, but not limited to, pharmaceutical compositions.

11 Claims, 8 Drawing Sheets

COMPOSITION, SYNTHESIS, AND USE OF A NEW CLASS OF ISONITRILES

CROSS-REFERENCE TO RELATED APPLICATIONS

This application claims priority under 35 U.S.C. §119(e) to U.S. Provisional Patent Application Ser. No. 61/942,843, filed Feb. 21, 2014, entitled "Composition, Synthesis, and Use of a New Class of Isonitriles", which is herein incorporated by reference.

GOVERNMENTAL INTEREST

This invention was made with Government support under grant no. AI051352 awarded by the National Institutes of Health. The Government has certain rights in the invention.

FIELD OF THE INVENTION

The invention relates to arylthio isonitrile compounds and their synthesis. The invention also relates to new arylthio isonitriles as intermediates for synthesizing isonitriles and nitriles.

BACKGROUND OF THE INVENTION

Isonitrile compounds and derivatives thereof are known in the art and can be used in various applications, including the fields of medicine and pharmaceuticals. For example, bioactive isonitrile-containing metabolites may be isolated and used to treat widespread infections and deaths caused by malaria. The spread of resistant strains and the rise in global temperatures has made the treatment of malaria one of the highest priorities of the World Health Organization for the third world and North America.

Various methods for synthesizing isonitrile compounds are also known in the art. For example, it is known that isonitriles can be synthesized by the reaction of primary amines with dichlorocarbene or by dehydration of a formamide with phosphorus oxychloride. The Hofmann synthesis is a chemical test for primary amines based on their reaction with potassium hydroxide and chloroform as dichlorocarbene precursors to isonitriles. Another route to producing isonitriles is by reaction of organolithium compounds with oxazoles and benzoxazoles. A further synthetic route toward isonitriles includes condensation of an amine with formic acid to yield a formamide, and subsequent dehydration of this formamide. Phosgene can be used in combination with the formamide to yield isonitriles.

Isonitriles are used as reactants in multi-component Ugi and Passerini condensations, heterocycle synthesis, in radical and Pauson-Khand reactions and as ligands and in medical imaging.

There are disadvantages associated with the known methods of synthesizing isonitriles. The deprotonation-alkylation syntheses are limited to special substrates and conjugate additions with alkylisonitriles are rare, extremely challenging, and require additional activation through further conjugation. There are little or no known methodologies that provide direct, rapid access to bioactive isonitrile-containing carbocycles. Multi-step sequences are often required. For example, the synthesis of an anti-fouling isonitrile may require as many as ten steps to convert a ketone into an isonitrile.

The commercial availability of isonitriles is limited and those that are commercially available can be expensive.

Thus, there is a need in the art to develop new connectivity methods, as well as, isonitriles having new structural diversity and fundamental reactivity patterns in alkylations and conjugate additions. Furthermore, it would be advantageous for the new methodologies of preparing isonitriles to include a minimum number of steps which are cost effective to perform and that result in high yields.

SUMMARY OF THE INVENTION

The invention relates in general to novel isonitrile compounds and, in particular, to novel arylthio isonitrile compounds. Further, the invention includes synthesis of the novel arylthio isonitrile compounds and their use as precursors or building blocks for preparing other isonitrile compounds.

One aspect of the invention provides a compound represented by a general structure of Formula I:

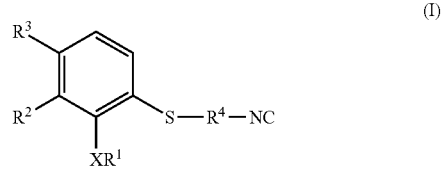

(I)

wherein, X is selected from oxygen, sulfur and nitrogen, $R^1$ is selected from alkyl and aryl, $R^2$ is selected from hydrogen and $XR^1$, $R^3$ is selected from hydrogen and $XR^1$, and $R^4$ is selected from alkyl and cyclic or polycyclic, aromatic or non-aromatic, structure, e.g., one or more rings, such as, but not limited to a cyclic six-membered ring. In certain embodiments, $R^1$ is selected from $C_1$-$C_6$ alkyl and aryl or $R^1$ is selected from $C_1$-$C_4$ alkyl and aryl. Further, in certain embodiments, $R^2$ and $R^3$ can come together to form a benzo ring.

In certain embodiments, the compound of the invention is represented by a general structure of Formula II:

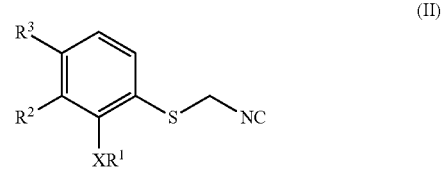

(II)

wherein X, $R^1$, $R^2$, and $R^3$ are as defined for Formula I.

In certain other embodiments, the invention provides a compound represented by a general structure of Formula III:

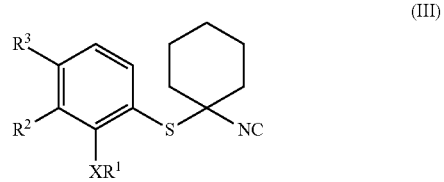

(III)

wherein X, $R^1$, $R^2$, and $R^3$ are as defined for Formula I.

In certain other embodiments, the invention provides a compound represented by a general structure of Formula IV:

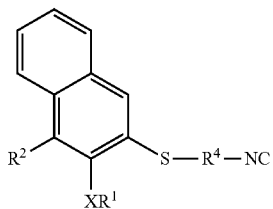

(IV)

wherein X, $R^1$, $R^2$ and $R^4$ are as defined for Formula I.

In another aspect, the invention provides a method of preparing an isonitrile including reacting a compound represented by a general structure of Formula III:

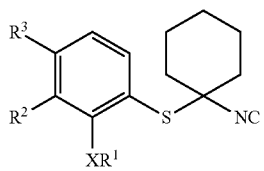

(III)

wherein, X, $R^1$, $R^2$ and $R^3$ are as defined for Formula I, with an electrophile in an exchange reaction to replace the arylthio group to form a compound represented by a general structure of Formula V or Formula VI:

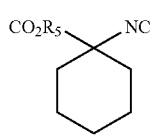

(V)

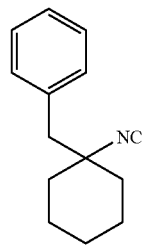

(VI)

wherein, $R^5$ is $C_1$-$C_4$ alkyl.

The electrophile may be selected from alkyl halides, acyl halides, carbonyl compounds and mixtures thereof. In certain embodiments, the electrophile is selected from diphenyl disulfide, methyl iodide, propyl bromide, propylene oxide, cyclohexanone, propyl iodide, cyclohexenone, and mixtures thereof.

BRIEF DESCRIPTION OF THE DRAWINGS

The various embodiments of the invention will be better understood when read with reference to the following figures.

DETAILED DESCRIPTION OF THE INVENTION

Figure 1:
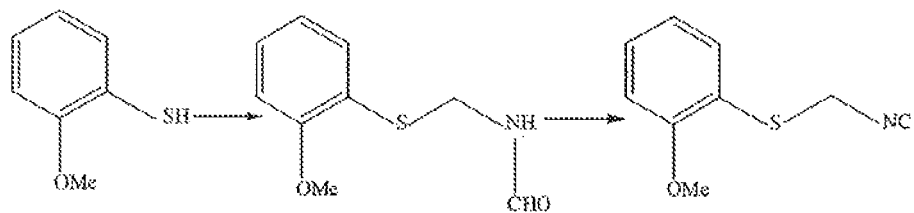
FIG. 1 illustrates a condensation/dehydration reaction scheme for preparing an arylthio isonitrile, in accordance with certain embodiments of the invention.

The invention relates in general to novel isonitrile compounds and, in particular, to new arylthio isonitriles that may be synthesized from readily available materials. The structures of the arylthio isonitriles are designed with the flexibility to have multiple substitution patterns.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, may contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between the incorporated material and the existing disclosure material.

The present disclosure describes several different features and aspects of the invention with reference to various exemplary non-limiting embodiments. It is understood, however, that the invention embraces numerous alternative embodiments, which may be accomplished by combining any of the different features, aspects, and embodiments described herein in any combination that one of ordinary skill in the art would find useful.

The invention relates to the development of a new arylthio isonitriles represented by a general structure of Formula I:

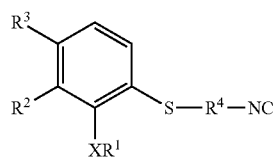

(I)

wherein, X is oxygen (O), sulfur (S) or nitrogen (N), $R^1$ is alkyl or aryl, $R^2$ is hydrogen (H) or $XR^1$, $R^3$ is hydrogen (H) or $XR^1$, and $R^4$ is alkyl or a cyclic or polycyclic, aromatic or non-aromatic, structure, e.g., one or more rings, such as, but not limited to a cyclic six-membered ring. In certain embodiments, $R^1$ is $C_1$-$C_6$ alkyl or aryl and in certain other embodiments, $R^1$ is $C_1$-$C_4$ alkyl or aryl. Further, in certain embodiments, $R^2$ and $R^3$ can come together to form a benzo ring.

In certain embodiments, the compound of the invention is represented by a general structure of Formula II:

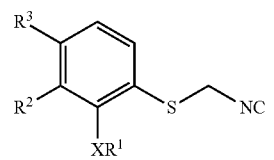

(II)

wherein X, $R^1$, $R^2$, and $R^3$ are as defined for Formula I.

For example, X, $R^1$, $R^2$ and $R^3$ can include the following combinations.

| X | $R^1$ | $R^2$ | $R^3$ |
|---|---|---|---|
| O | $CH_3$ | H | H |
| O | $CH_3$ | $OCH_3$ | H |
| O | $CH_3$ | $OCH_3$ | $OCH_3$ |
| O | Phenyl | H | H |
| S | $CH_3$ | H | H |
| S | $CH_3$ | $OCH_3$ | H |
| S | $CH_3$ | $OCH_3$ | $OCH_3$ |
| S | Phenyl | H | H |
| N | $CH_3$ | H | H |
| N | $CH_3$ | $OCH_3$ | H |
| N | $CH_3$ | $OCH_3$ | $OCH_3$ |
| N | Phenyl | H | H |

In certain other embodiments, the compound of the invention is represented by a general structure of Formula III:

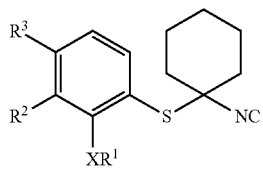

(III)

wherein X, $R^1$, $R^2$, and $R^3$ are as defined for Formula I.

In certain other embodiments, the compound of the invention is represented by a general structure of Formula IV:

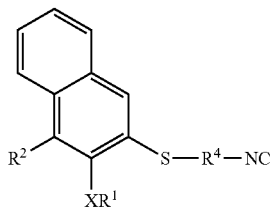

(IV)

wherein X, $R^1$, $R^2$, and $R^4$ are as defined for Formula I.

The compounds of the invention may be readily synthesized using organic chemistry techniques. The syntheses of various embodiments of the isonitrile precursors and products are described herein. It should be noted that the featured embodiments are intended to be exemplary and are in no way limiting to the scope of the isonitrile precursors and products as described herein. For example, the compounds of Formulas I and II can be prepared according to certain embodiments of the invention. In general, condensation and dehydration reactions may be conducted to form the compounds of Formulas I and II. These compounds then may be used as precursors or building blocks to form other arythio isonitriles. In certain embodiments, compounds represented by Formula I and Formula II can be subjected to double alkylation reactions to form the arylthio isonitrile represented by Formula III. The compounds of Formulas III and IV then may be used as precursors or building blocks to form other isonitrile compounds. For example, compounds represented by Formula III can be subjected to an exchange reaction to form the isonitriles represented by the general structures of Formulas V and VI:

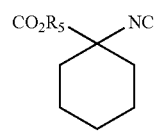

(V)

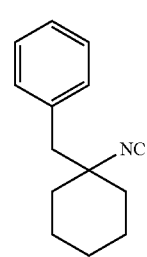

(VI)

wherein, $R^5$ is $C_1$-$C_4$ alkyl.

Certain specific synthesis examples are discussed in detail in FIGS. 1, 2, 3 and 4.

Compounds represented by the general structure of Formula II herein can be prepared by known organic reactions, such as, Mannich condensation reactions. FIG. 1 shows a reaction scheme for preparing arylthio isonitrile of Formula II, in accordance with certain embodiments of the invention, wherein X is oxygen, $R^1$ is methyl and, each of $R^2$ and $R^3$ is hydrogen. As shown in FIG. 1, o-methoxy-thiophenol (aryl thiol) is reacted with formamide in formic acid and toluene to form an intermediate product wherein the hydrogen molecule of the o-methoxy-thiophenol is replaced with an isonitrile group. It is contemplated and understood that other aryl thiols can be reactants, such as, but not limited to, those shown in Table 1. Further, it is contemplated that other suitable acids and solvents known in the art can be used. Non-limiting examples of suitable acids include, but are not limited to, acetic acid, proprionic acid, trifluoroacetic acid, chloroacetic acid, toluenesulfonic acid, camphor sulfonic acid, and mixtures thereof. Non-limiting examples of suitable solvents include, but are not limited to, formaldehyde, dimethyl formamide, dimethylacetamide, hexamethylphosphoramide, dimethylsulphoxide, tetrahydrofuran and mixtures thereof.

The intermediate product then undergoes a dehydration reaction to remove the water molecule, such that NH—CHO in the intermediate product is NC in the final isonitrile product. Various dehydration methods and processes can be used. In accordance with certain embodiments of the invention and as shown in FIG. 1, the intermediate product is reacted with phosphorus oxychloride in diisopropylamine to form an (isocyanomethyl)(2-methoxyphenyl)sulfane product (represented by the general structure of Formula II herein). It is contemplated and understood that other isonitriles can be synthesized by a dehydration reaction, such as, but not limited to, those shown in Table 1. Further, it is contemplated that other suitable solvents and dehydrating agents known in the art can be used. Non-limiting examples of suitable solvents include, but are not limited to, dichoromethane, toluene, chloroform and mixtures thereof. Non-limiting examples of suitable dehydrating agents include, but are not limited to, triphenylphosphine dichloride, triphenylphosphine dibromide, triphenylphosphine/carbon tetrabromide, sulfonyl chloride, oxalyl chloride and mixtures thereof. The dehydration step can be conducted at various temperatures and is typically carried out at a temperature within a range from −30° C. to 0° C.

The resulting product may be purified by conventional purification methods and processes known in the art such as, but not limited to, vacuum distillation, flash chromatography, preparative thin layer chromatography and radial chromatography.

Figure 2:
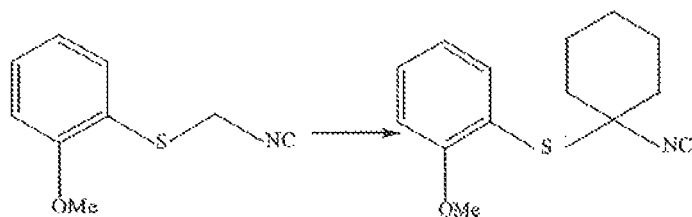
FIG. 2 illustrates a double alkylation reaction scheme for preparing an arylthio isonitrile, in accordance with certain embodiments of the invention.

As shown in FIG. 2, compounds represented by the general structure of Formula II herein may be used as precursors or building blocks to form other arylthio isonitriles. For example, compounds of Formula II can be used to prepare arylthio isonitriles represented by the general structure of Formula III herein, wherein X is oxygen, $R^1$ is methyl and, each of IV and $R^3$ is hydrogen. In particular, in FIG. 2, the (isocyanomethyl)(2-methoxyphenyl)sulfane product as shown in FIG. 1 undergoes an alkylation reaction to replace the $CH_2$ group bridging the arylthio and the isonitrile to form a (1-isocyanocyclohexyl)(2-methoxyphenyl)sulfane product (represented by the general structure of Formula III herein). As shown in FIG. 2, the (isocyanomethyl)(2-methoxyphenyl)sulfane reactant is reacted with the dihalide 1,5-dibromopentane in sodium hydride and dimethyl formamide (DMF). The sodium hydride is typically present in an amount in the range from 2 to 5 equivalents. The alkylation reaction can be conducted at various temperatures and typically the temperature is in the range from −10° C. to room temperature. The time for carrying out the alkylation can also vary and typically is carried out in a time period in the range from 10 hours to 72 hours. It is contemplated and understood that other arylthio isonitriles can be synthesized by an alkylation reaction, such as, but not limited to, those shown in Table 1. Further, it is contemplated that other bases known in the art for use in organic synthesis can be used, such as but not limited to, sodium hydroxide, potassium hexamethyldisilazide, lithium amide, sodium amide and mixtures thereof. Further, it is contemplated that any solvent can be used that is compatible with the base, e.g., sodium hydride, such as but not limited to, dimethylacetamide, hexamethylphosphoramide, dimethylsulphoxide, tetrahydrofuran, toluene and mixtures thereof. It is also contemplated that other dihalide compounds known in the art can be used. Non-limiting examples of suitable dihalides include, but are not limited to, 1,3-dihalopropane, 1,4-dihalobutane, 1,5-dihalopentane, 1,6-dihalohexane and mixtures thereof.

The resulting product may be purified by conventional purification methods and processes known in the art such as, but not limited to, vacuum distillation, flash chromatography, preparative thin layer chromatography and radial chromatography.

Figure 3:
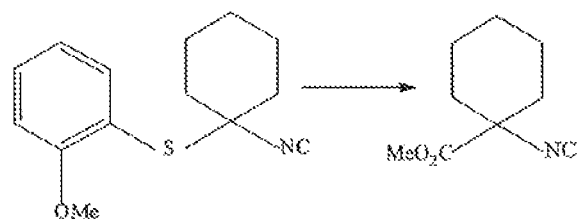
FIG. 3 illustrates an exchange reaction scheme for preparing an arylthio isonitrile, in accordance with certain embodiments of the invention.
Figure 4:
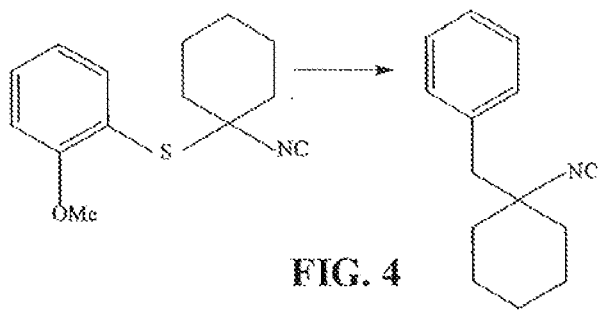
FIG. 4 illustrates an exchange reaction scheme for preparing an arylthio isonitrile, in accordance with certain embodiments of the invention.

As shown in FIGS. 3 and 4, compounds represented by the general structure of Formula III herein may be used as precursors or building blocks to form other isonitriles. For example, was shown in FIG. 3, compounds represented by the general structure of Formula III can be reacted with an electrophile to prepare isonitriles represented by the general structure of Formula V, wherein $R^5$ is methyl, herein. In particular, in FIG. 3, the (1-isocyanocyclohexyl)(2-methoxyphenyl)sulfane product as shown in FIG. 2 undergoes an exchange reaction to replace thioaryl with a methoxycarbonyl group. As shown in FIG. 3, (1-isocyanocyclohexyl)(2-methoxyphenyl)sulfane is reacted with the electrophile methyl cyanoformate in n-butyl lithium and tetrahydrofuran (THF) to form methyl 1-isocyanocyclohexane-1-carboxylate. It is contemplated and understood that other arylthio isonitriles may be synthesized by an exchange reaction, such as, but not limited to, those shown in Table 1.

As shown in FIG. 4, compounds represented by the general structure of Formula III can be reacted with an electrophile to prepare isonitriles represented by the structure of Formula VI herein. In particular, in FIG. 4, an exchange reaction includes reacting (1-isocyanocyclohexyl)(2-methoxyphenyl)sulfane with the electrophile benzyl bromide in n-butyl lithium and THF to form 1-isocyanocyclohexane-1-benzyl.

For the exchange reactions, it is contemplated that various other bases and solvents can be used provided that the solvent is compatible with the base. Suitable solvents include, but are not limited to, ethyl ether, dioxane, methyltetrahydrofuran, hexane, cyclohexane, pentane and mixtures thereof. Further, it is contemplated that various other suitable electrophiles may be used in the exchange reaction, such as, but not limited to, alkyl halides, acyl halides and carbonyl compounds. Non-limiting examples of suitable electrophiles include, but are not limited to, diphenyl disulfide, methyl iodide, propyl bromide, propylene oxide, cyclohexanone, propyl iodide, cyclohexenone, and mixtures thereof.

The exchange reaction can be conducted at various temperatures and is typically in the range from −30° C. to −78° C.

As mentioned herein, Table 1 shows various, e.g., suitable, aryl thiols for use in the invention, arylthio isonitriles synthesized by suitable formamide synthesis and dehydration methods, arylthio isonitriles synthesized by suitable alkylation methods, and suitable exchange reactions for arylthio isonitriles.

TABLE 1

Aryl Thiols

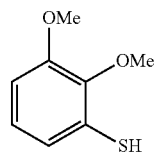 [SMILES: COc1cccc(S)c1OC]
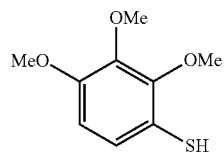
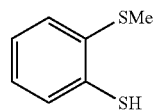
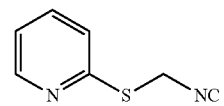

Aryl Isonitriles Synthesized by Formamide and Dehydration Method

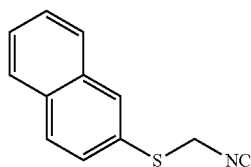
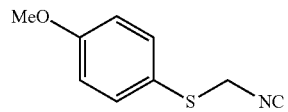
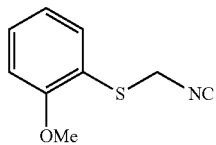
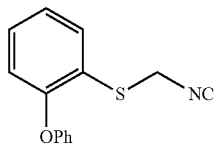
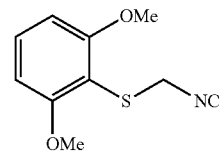
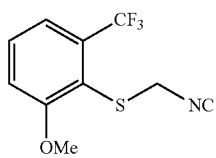
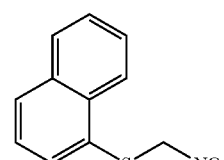
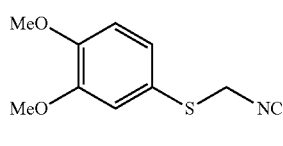
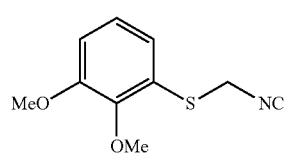

TABLE 1-continued
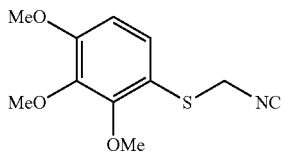
Arylthio Isonitriles Synthesized by Alkylation Method
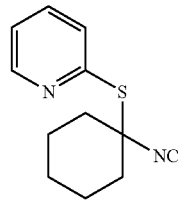 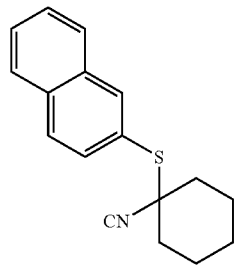
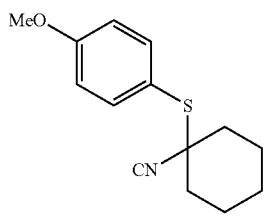 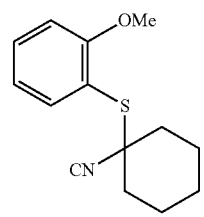
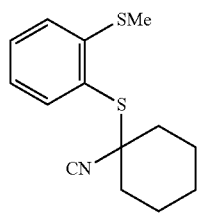 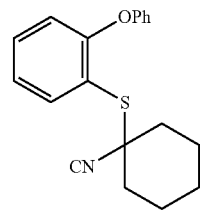
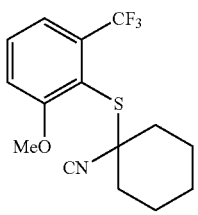 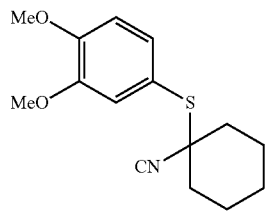
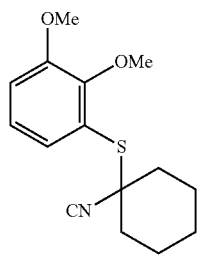 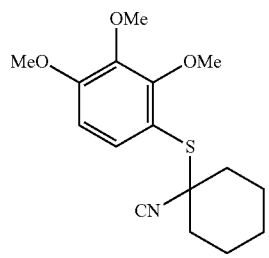

TABLE 1-continued
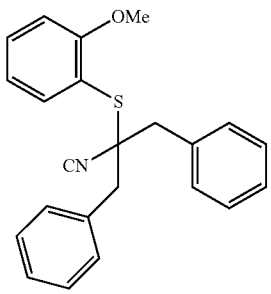
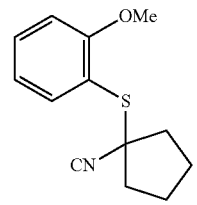
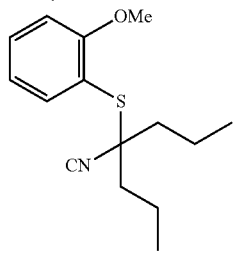
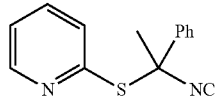
Arylthio Isonitriles Syntesized by Exchange Reactions
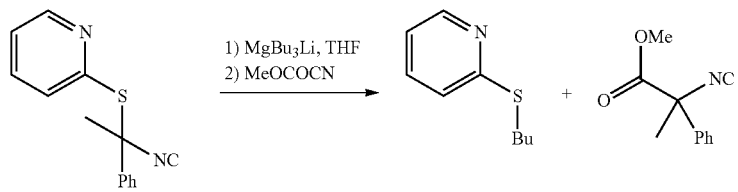
1) MgBuLi @ -78, 5 min.      29%     13%
rhen
2) MeOCOCN, 15 min
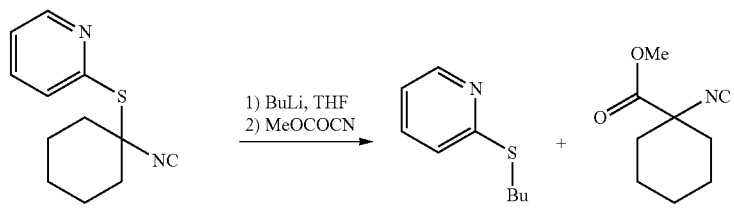
315 MgBu3•Li @ −78, 5 min.     traces     --
or
326 BuLi @ −78, 5 min.     ??     --
then
2) MeOCOCN, 5 min
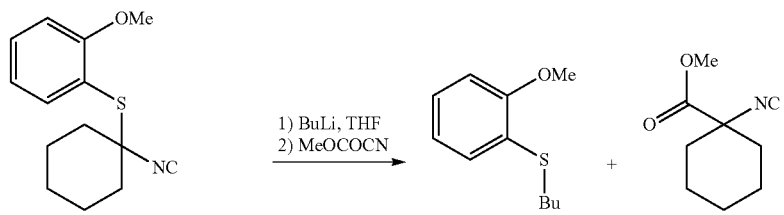
414 1) BuLi @ -78° C., 5 min?     4  :  1
    2) MeOCN -78° C., 10 min
428 1) BuLi @ -78° C., 10 min?     ~90%     45%
    2) MeOCN @ -78° C., 2 h and
       1 h @ 0° C.
691 1) BuLi @ -70° C., 15 min     3  :  1
    2) MeOCN @ -70 to -65° C. 0.5 h,
       the 90 min @ 0° C.

TABLE 1-continued
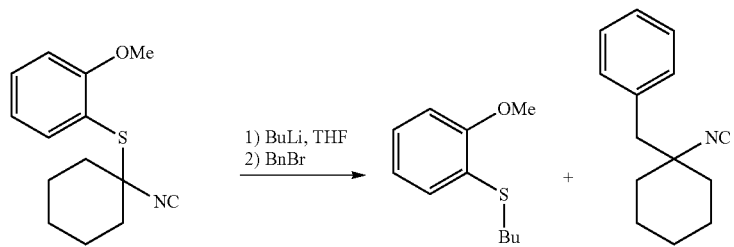
1) BuLi @ 78° C., 15 min. then
2) BnBr, 30 min @ -70 to -65° C., then 90 min @ 0° C.
>95%  75%
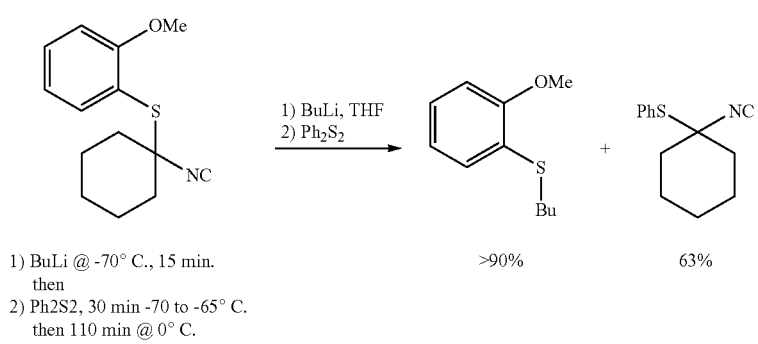
1) BuLi @ -70° C., 15 min. then
2) Ph2S2, 30 min -70 to -65° C. then 110 min @ 0° C.
>90%  63%
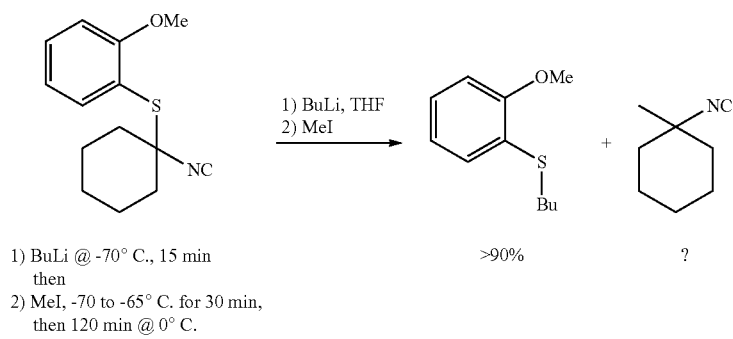
1) BuLi @ -70° C., 15 min then
2) MeI, -70 to -65° C. for 30 min, then 120 min @ 0° C.
>90%  ?
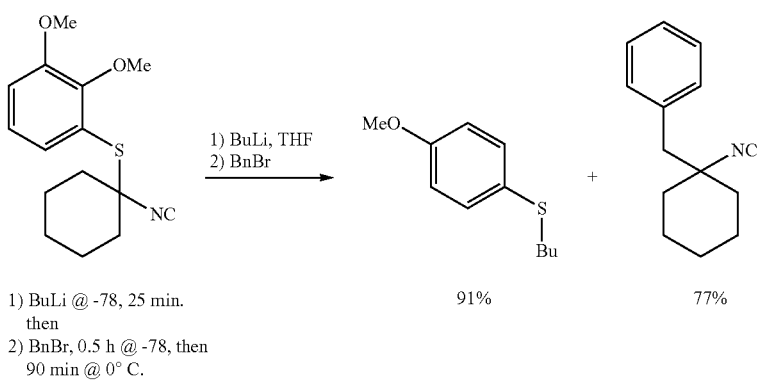
1) BuLi @ -78, 25 min. then
2) BnBr, 0.5 h @ -78, then 90 min @ 0° C.
91%  77%

TABLE 1-continued
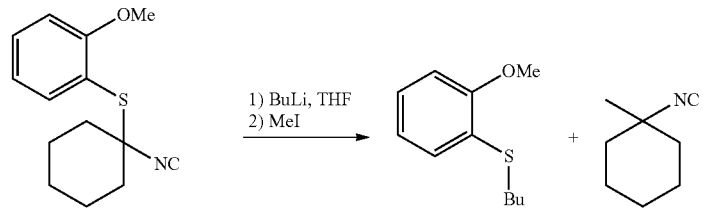
1) BuLi @ -70° C., 15 min
   then
2) MeI, -70 to -65° C. for 30 min,
   then 120 min @ 0° C.
>90%          ?
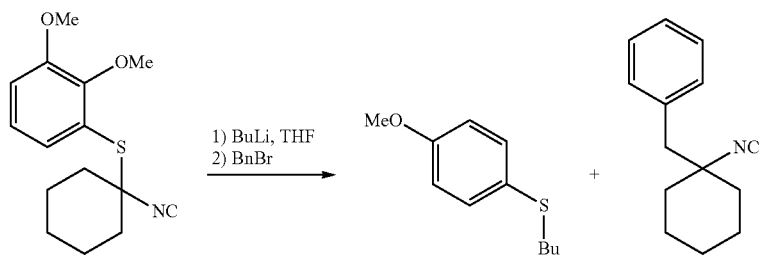
1) BuLi @ -78, 25 min.
   then
2) BnBr, 0.5 h @ -78, then
   90 min @ 0° C.
91%          77%
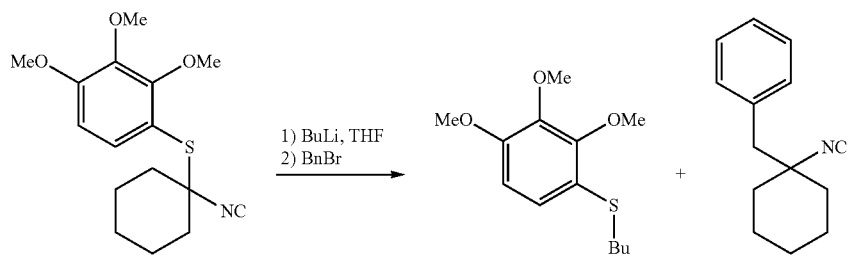
1) BuLi @ -78, 15 min.
   then
2) BnBr, 0.5 h @ -78, then
   0.5 h @ 0° C.
>90%          not detected
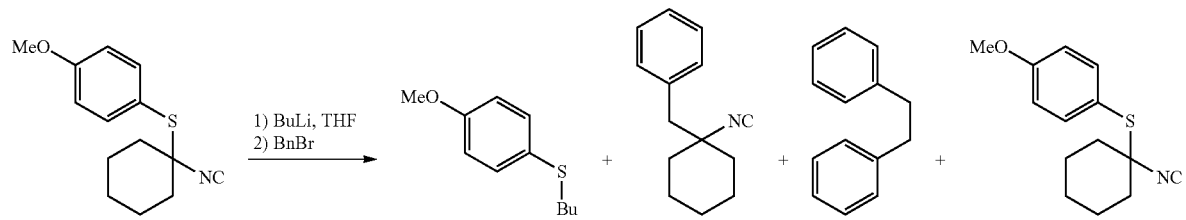
1) BuLi @ -78, 15 min.
   then
2) BnBr, 0.5 h @ -78, then
   1 h @ 0° C.
<10%     not detected     major TABLE 1-continued
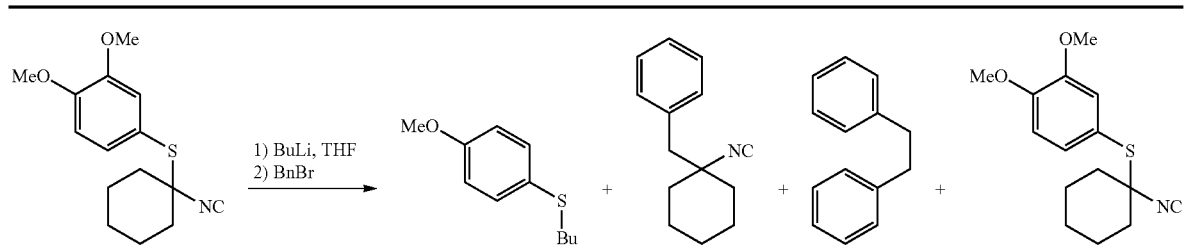
1) BuLi @ -78, 15 min. then
2) BnBr, 0.5 h @ -78, then 1 h @ 0° C.
<20%   not detected   major
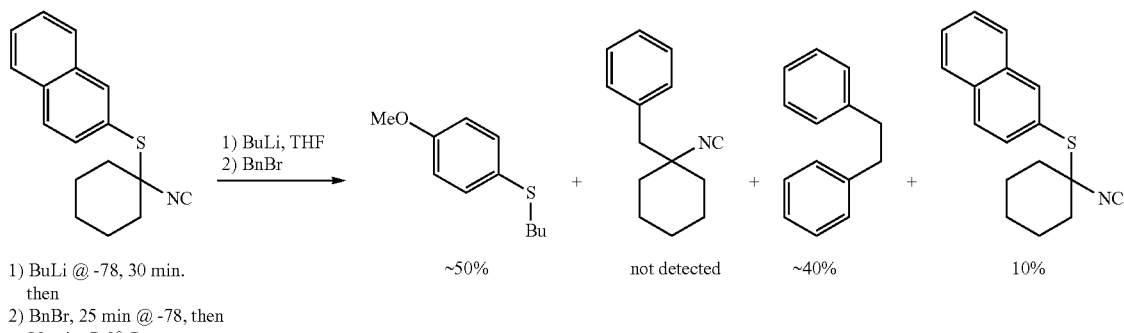
1) BuLi @ -78, 30 min. then
2) BnBr, 25 min @ -78, then 80 min @ 0° C.
~50%   not detected   ~40%   10%
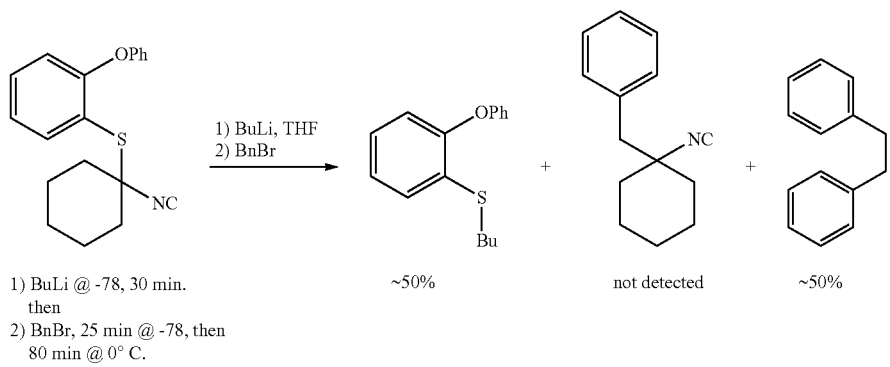
1) BuLi @ -78, 30 min. then
2) BnBr, 25 min @ -78, then 80 min @ 0° C.
~50%   not detected   ~50%
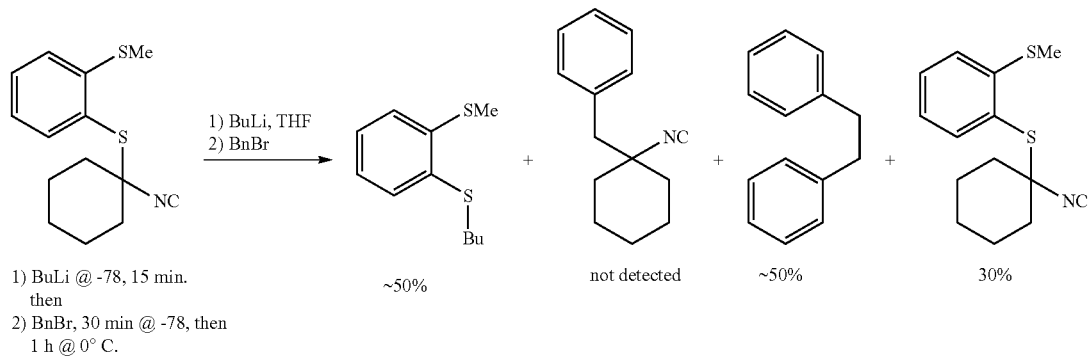
1) BuLi @ -78, 15 min. then
2) BnBr, 30 min @ -78, then 1 h @ 0° C.
~50%   not detected   ~50%   30%

TABLE 1-continued

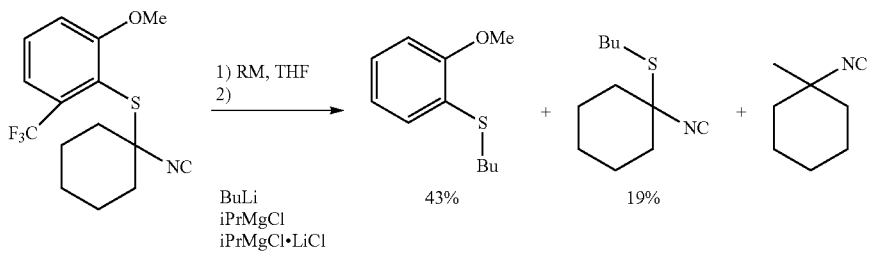

BuLi
iPrMgCl
iPrMgCl·LiCl

Moreover, other embodiments of the invention will be apparent to those skilled in the art from consideration of the specification and practice of the invention disclosed herein. It is intended that the specification be considered as exemplary only. Furthermore, the following examples are meant to be illustrative of certain embodiments of the invention and are not intended to be limiting as to the scope of the invention.

EXAMPLES

The following examples were conducted in support of the invention. Example 1 is directed to Mannich condensation/dehydration reactions for the synthesis of (isocyanomethyl)(2-methoxyphenyl)sulfane. Example 2 is directed to double alkylation-cyclization for the synthesis of (1-isocyanocyclohexyl)(2-methoxyphenyl)sulfane. Examples 3 and 4 are directed to exchange-functionalization for the synthesis of methyl 1-isocyanocyclohexane-1-carboxylate and 1-isocyanocyclohexane-1-benzyl. These examples, as well as Examples 5-50, are meant to be illustrative only of certain embodiments of the invention.

Example 1

Mannich Condensation/Dehydration for the Synthesis of (isocyanomethyl)(2-methoxyphenyl)sulfane

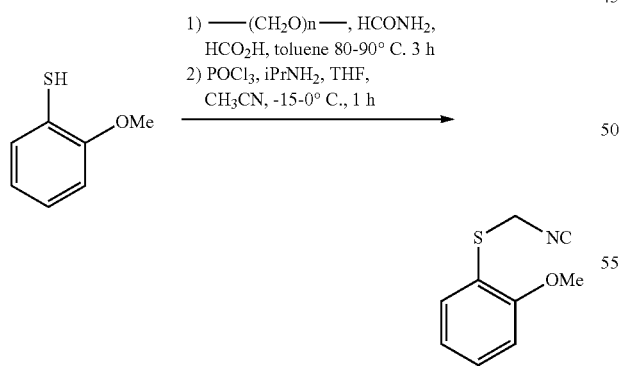

A 20 mL microwave Biotage® vial was charged with o-methoxy-thiophenol (2.0 g, 14.3 mmol, 1 eq), paraformaldehyde (2.14 g, 71.3 mmol, 5 eq) and capped. The vial was purged with $N_2$ and then formamide (3.4 mL, 85.6 mmol, 6 eq), formic acid (2.2 mL, 57.1 mmol, 4 eq), and toluene (6 mL) were added consecutively via syringe. The vial was irradiated for 1 hour at 80° C., the vial was vented, and then 2 hours at 90° C., using a Biotage® Initiator microwave reactor (Radiation absorption set to NORMAL). The contents were poured on water/ice (10 mL). The mixture was extracted four times with ethyl acetate. The combined organic extracts were washed with brine and dried ($Na_2SO_4$). The solvents were removed in vacuo and then high vacuum for 2 hours to leave a white solid with sufficient purity for the next step.

A 25 mL round bottom flask, containing the material of the previous reaction, was dissolved with acetonitrile (11 mL) and tetrahydrofuran (22 mL). The flask was cooled down to −15 to −10° C. using an ice/acetone/$NH_4Cl$ bath. Diisopropylamine (14 mL, 100 mmol, 9.3 eq) was added drop wise, followed by prompt drop wise addition of phosphorus oxychloride (3.29 mL, 35.3 mmol, 3.3 eq). The mixture was kept between −15° C. and 0° C. for 1 hour before the contents were poured to a $NaHCO_3$ (sat)/ice mixture (10 mL). The organic phase was separated and the aqueous was extracted twice with DCM. The combined organic extracts were washed with brine and dried ($Na_2SO_4$). The solvents were removed in vacuo leaving an orange oil. The crude product was purified by radial chromatography using a gradient (95/5 to 80/20 hexane/ether) on a 2 mm thick $SiO_2$ plate obtaining 1.34 g of a colorless oil (70% yield, 2 steps).

$^1$H NMR (400 MHz, Chloroform-d) δ 7.53 (dd, J=7.7, 1.7 Hz, 1H), 7.38 (ddd, J=8.1, 7.4, 1.7 Hz, 1H), 6.99 (td, J=7.6, 1.2 Hz, 1H), 6.94 (dd, J=8.3, 1.2 Hz, 1H), 4.57 (s, 2H), 3.91 (s, 3H). $^{13}C$ NMR (101 MHz, Chloroform-d) δ 158.86, 134.81, 130.98, 121.47, 118.74, 111.26, 55.97, 42.87. IR (ATR) 2137 $cm^{-1}$.

Example 2

Double Alkylation-Cyclization for the Synthesis of (1-isocyanocyclohexyl)(2-methoxyphenyl)sulfane

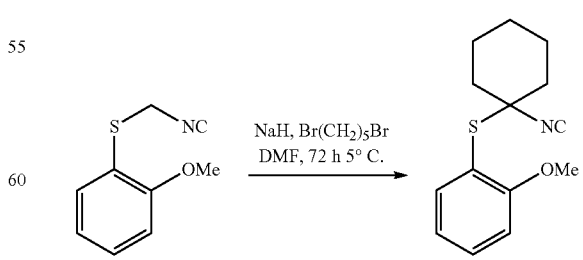

A 50 mL round-bottomed flask equipped with a magnetic stir bar and a septum was flame dried. The flask was charged with an excess of sodium hydride (174 mg, 4.35 mmol, 3 eq), capped and purged with dry $N_2$. The flask was cooled to 0° C. and charged with DMF (14.5 mL, 0.1 M) and 1,5-dibromopentane (0.2 mL, 1.45 mmol, 1 eq). Then, (isocyanomethyl)(2-methoxyphenyl)sulfane (260 mg, 1.45 mmol) was added drop wise and the resulting mixture was allowed to stir for 18 hours at 5° C. The mixture was poured into water/ice and the mixture was extracted three times with ethyl acetate. The combined organic extracts were washed with brine and dried ($Na_2SO_4$). The solvents were removed in vacuo leaving a yellowish oil. The crude product was purified by radial chromatography separation using an eluent of 95/5 Hex/ether on a 1 mm thick $SiO_2$ plate, obtaining 220 mg of (1-isocyanocyclohexyl)(2-methoxyphenyl)sulfane as an colorless oil (61% yield).

$^1$H NMR (400 MHz, Chloroform-d) δ 7.67 (dd, J=7.5, 1.8 Hz, 1H), 7.43 (ddd, J=8.4, 7.5, 1.8 Hz, 1H), 6.99 (td, J=7.5, 1.3 Hz, 1H), 6.96 (dd, J=8.3, 1.2 Hz, 1H), 3.87 (s, 3H), 1.97 (bd, J=13.1, 2H), 1.82-1.49 (m, 7H), 1.35-1.21 (m, 1H). $^{13}$C NMR (100 MHz, Chloroform-d) δ 161.21, 156.52, 139.87, 132.25, 121.09, 116.69, 111.27, 68.38 (t, J=5.1 Hz), 55.84, 38.01, 24.68, 22.31. IR (ATR) 2120 cm$^{-1}$. HRMS (ESI) calculated for $C_{14}H_{17}NOS$ 270.0923. found 270.0916 $(M+Na)^+$.

Example 3

Exchange-Functionalization for the Synthesis of methyl 1-isocyanocyclohexane-1-carboxylate

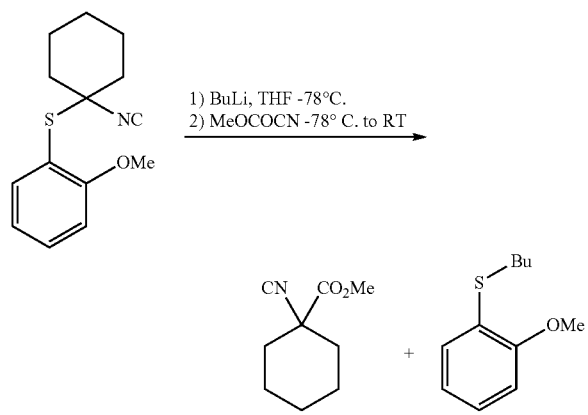

A 25 mL round-bottomed flask equipped with a magnetic stir bar and a septum was flame dried and purged with dry $N_2$. The flask was charged (1-isocyanocyclohexyl)(2-methoxyphenyl)sulfane (50 mg, 0.21 mmol, 1 eq) and THF (6.7 mL, 0.03 M). The solution was cooled to a temperature of −78° C. and n-BuLi (1.0 eq) was then added drop-wise. The resulting mixture was stirred for about 10 minutes. Methyl cyanoformate (1.5 eq) was added in one portion and stirring was continued at −78° C. for 2 hours, and the reaction was allowed to warm to room temperature in a 1 hour interval. The mixture was poured into water/ice and the phases separated. The organic was collected and the aqueous was extracted with ethyl acetate twice. The combined organic extracts were washed with brine and dried ($Na_2SO_4$). The solvents were removed in vacuo leaving a yellow oil. Radial chromatography separation using a 1 mm thick $SiO_2$ plate and an eluent gradient of 95/5 to 90/10 Hex/Ether, yielded 15 mg of methyl 1-isocyanocyclohexane-1-carboxylate as a colorless oil (44% yield) and the expected aryl-butyl thioether.

Example 4

Exchange-Functionalization for the Synthesis of 1-isocyanocyclohexane-1-benzyl

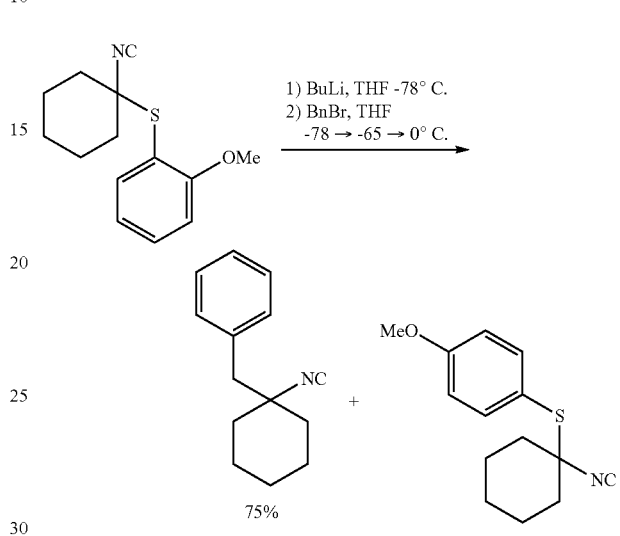

A 25 mL Schlenk flask equipped with a magnetic stir bar and a septum was flame dried and purged with dry $N_2$. The flask was charged with (1-isocyanocyclohexyl)(2-methoxyphenyl)sulfane (63 mg, 0.25 mmol, 1 eq) and tetrahydrofuran (5.1 mL, 0.05 M). The solution was cooled to a temperature of −78° C. and n-BuLi (1.05 eq) was added drop-wise. The resulting mixture was stirred for 15 minutes at the same temperature. Benzyl bromide (52.3 mg, 0.3 mmol) was dissolved in dry tetrahydrofuran (0.3 mL) and added in one portion with continued stirring allowing the temperature to increase to −65° C. in a 30 minute interval, and then, for an additional 1.5 hours at a temperature of 0° C. The reaction was then poured on cold half-saturated $NaHCO_3$. The organic was collected and the aqueous was extracted with ethyl acetate twice. The combined organic extracts were washed with brine and dried ($Na_2SO_4$). The solvents were removed in vacuo and the residue was separated by $SiO_2$ radial chromatography (1 mm thickness rotor) to give 38 mg of a colorless oil (75%).

Example 5

Preparation of 2,3-dimethoxybenzenethiol

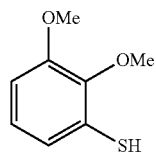 [SMILES: COc1cccc(S)c1OC]

A hexane solution of BuLi (5.1 mL, 7.96 mmol) was added in one portion to neat veratrole (1.0 g, 7.24 mmol). After 10 min, tetramethylethylenediamine (11 µL, 0.07 mmol) was added dropwise. After stirring for 30 min at room temperature, elemental sulfur (232 mg, 7.23 mmol) was added in one portion under a nitrogen blanket. After stirring for 20 min, the reaction was diluted with cold water (15 mL) and was stirred at room temperature for 10 min before adding Et$_2$O (10 mL). The organic layer was discarded and the aqueous was extracted once again with Et$_2$O (10 mL). The aqueous layer was then acidified with HCl 2M until pH~1. The mixture was extracted with Et$_2$O (×3) and dried (Na$_2$SO$_4$). After removal of the volatiles, the crude was purified by filtration on a SiO$_2$ plug using hexanes: Et$_2$O (95:5 to 90:10) as eluent to yield 0.7 g (57%) as a colorless oil. $^1$H NMR (500 MHz, Chloroform-d) δ 6.94-6.90 (m, 1H), 6.84 (dd, J=8.0, 1.5 Hz, 1H), 6.69 (dd, J=8.2, 1.4 Hz, 1H), 3.85 (s, 2H), 3.84 (s, 3H). $^{13}$C NMR (125 MHz, Chloroform-d) δ 153.11, 144.65, 127.13, 124.50, 120.93, 109.60, 59.88, 55.89

Example 6

Preparation of 2,3,4-trimethoxybenzenethiol

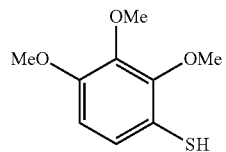

Preparation was in accordance with 2,3-dimethoxybenzenethiol, from 2,3,4-trimethoxybenzene (1.5 g, 8.92 mmol). After removal of the volatiles, the crude was purified by SiO$_2$ column chromatography using gradient (hexanes: EtOAc 95:5 to 90:10) to yield 1.01 g (57%) as an oil. $^1$H NMR (400 MHz, Chloroform-d) δ 6.95 (d, J=8.7 Hz, 1H), 6.59 (d, J=8.7 Hz, 1H), 3.91 (s, 3H), 3.87 (s, 3H), 3.83 (s, 3H), 3.64 (s, 1H). 13C NMR (101 MHz, Chloroform-d) δ 152.09, 150.10, 143.06, 123.70, 117.10, 108.29, 61.01, 60.49, 56.24. IR (ATR) 2937, 2837, 2566, 1584, 1589, 1410, 1479, 1224, 1089, 1010, 793 cm$^{-1}$.

Example 7

Preparation of 2-(methylthio)benzenethiol

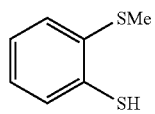

A THF solution (5 mL) of 2-bromothiophenol (3 g, 14.77 mmol) was added dropwise to a THF slurry (12 mL) of magnesium turnings (0.467 g, 19.20 mmol) that had been previously activated through the addition of 1,2-dibromoethane (127 μL, 1.47 mmol). The flask was gently heated with a heat gun, while avoiding boiling. After 30 min, the flask was irradiated at room temperature in an ultrasonic cleaning bath for 2 h to provide a THF solution of the Grignard reagent. Elemental sulfur (0.663 g, 20.68 mmol) was added in one portion, under a N$_2$ blanket, to the 0° C. solution of the (2-(methylthio)phenyl)magnesium bromide. After 30 min, lithium aluminum hydride powder (0.27 g, 7.39 mmol) was added in very small portions. After 30 min, the reaction was diluted with cold, aqueous, saturated NH$_4$Cl (20 mL) and then aqueous citric acid 2M (5 mL). The mixture was extracted with dichloromethane (3×30 mL) and after the removal of volatiles, the resulting oil was dissolved in 100 mL of 5% NaOH. The solution was then extracted with Et$_2$O (2×25 mL). The aqueous layer was acidified with HCl$_{(conc)}$ and extracted with Et$_2$O (3×50 mL). After removal of the volatiles, 1.132 g was obtained as a slightly purple translucid oil (49%). $^1$H NMR (500 MHz, Chloroform-d) δ 7.30 (dd, J=7.7, 1.5 Hz, 1H), 7.25 (dd, J=7.9, 1.4 Hz, 1H), 7.12 (ddd, J=7.9, 7.4, 1.4 Hz, 1H), 7.05 (td, J=7.5, 1.4 Hz, 1H), 3.99 (s, 1H), 2.45 (s, 3H). $^{13}$C NMR (126 MHz, Chloroform-d) δ 136.56, 132.22, 129.93, 128.25, 126.42, 126.24, 16.85.

Example 8

General Formamide Synthesis—Conventional Heating

Paraformaldehyde (4 eq), formamide (7.5 eq) and formic acid (5 eq) were sequentially added to neat methyl sulfinate (1 eq), and then the flask was immersed in a preheated oil bath (90-100 C). After 2-3 h the mixture was diluted with cold water. If the material precipitated, the crude formamide was isolated by filtration; otherwise, the mixture was extracted with EtOAc (×4). The combined organic extract was washed once with brine, dried (Na$_2$SO$_4$), and concentrated to provide the crude formamide. Chloroform was added prior to reconcentration in vacuo to act as a chaser in removing other volatile reagents. The material was dried for 2 h under high vacuum before performing the dehydration.

Example 9

General Dehydration Method

Dry diisopropylamine or dry triethylamine (9.3 equiv) were sequentially added dropwise to a −20° C., THF: acetonitrile solution (0.3 M, 2:1 mixture) of the crude formamide (1 eq). The temperature was maintained below −10° C. during the addition of both reagents. After 1 h, while maintaining the temperature below −10° C., the reaction was diluted with cold, aqueous NaHCO$_3$ and then the phases were separated. The mixture was extracted with dichloromethane (×4), the combined organic extract was washed with brine, dried (Na$_2$SO$_4$), and concentrated to provide the crude isonitrile. The crude isonitrile was filtered through a SiO$_2$ plug (10×50 mm) using hexanes:Et$_2$O (90:10 to 70:30) and then purified by SiO$_2$ flash chromatography or SiO$_2$ radial chromatography to provide the pure isonitrile.

Example 10

Preparation of 2-((isocyanomethyl)thio)pyridine

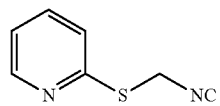

To a cold solution of MeNC (0.1 g, 2.44 mmol) a BuLi solution in hexanes (0.95 mL, 2.56 mmol) was added dropwise. After stirring for 1 h at the same temperature, a solution of 2,2'-dipyridildisulfide (0.64 g, 2.92 mmol) in tetrahydrofuran (3 mL) was added in one portion. After 15 min, reaction was diluted with cold NaH$_2$PO$_4$ 10% (25 mL) and the mixture extracted with EtOAc (×3). 0.160 g (44%) were obtained as an oil after purification by DIOL column chromatography using hexanes:Et$_2$O 95:5. $^1$H NMR (400 MHz, Chloroform-d) δ 8.52 (ddd, J=5.0, 1.9, 1.0 Hz, 1H), 7.59 (td, J=7.7, 1.8 Hz, 1H), 7.23 (dt, J=8.0, 1.0 Hz, 1H), 7.11 (ddd, J=7.4, 4.9, 1.1 Hz, 1H), 5.07 (s, 2H). $^{13}$C NMR (100 MHz, Chloroform-d) δ 158.31, 153.72, 149.94, 136.91, 122.78, 121.11, 39.09 (t, J=6.8 Hz). IR (ATR) 2994, 2141, 1578, 1455, 1416, 1120, 924, 757, 730 cm$^{-1}$.

Example 11

Preparation of (isocyanomethyl)(naphthalen-2-yl)sulfane

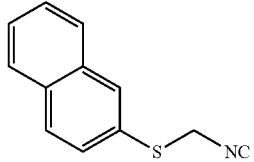

The sulfanyl formamide was prepared from naphthalene-2-thiol (2 g, 12.48 mmol) according to the general formamide synthesis method (2.5 h at 95° C.). The crude formamide was dehydrated following the general method with iPr$_2$NH to provide 1.652 g (66%, 2 steps) of the product as a white solid after purification by SiO$_2$ radial chromatography using gradient (hexanes:EtOAc 90:10 to 70:30). mp 81-81.5° C. $^1$H NMR (400 MHz, Chloroform-d) δ 8.08 (s, 1H), 7.89-7.83 (m, 3H), 7.60 (dt, J=8.6, 1.3 Hz, 1H), 7.59-7.49 (m, 2H), 4.62 (s, 2H). $^{13}$C NMR (100 MHz, Chloroform-d) δ 159.82, 133.63, 133.09, 132.25, 129.39, 129.04, 128.90, 127.82 (d, J=1.2 Hz), 127.11, 126.96, 45.14 (t, J=6.4 Hz). IR (ATR) 3053, 2977, 2145, 1586, 1502, 1423, 1199, 1076, 916, 811, 732 cm$^{-1}$.

Example 12

Preparation of (isocyanomethyl)(4-methoxyphenyl)sulfane

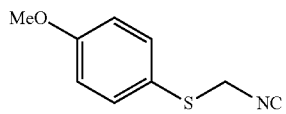

The sulfanyl formamide (1.59 g, 75%) was prepared from 4-methoxybenzenethiol (1.5 g, 10.70 mmol) according to the general formamide synthesis method (2.5 h at 95° C.). The crude formamide was dehydrated following the general method with iPr$_2$NH to provide 1.09 g (57%, 2 steps) as an amber oil after purification on SiO$_2$ radial chromatography (4 mm thickness rotor) using hexanes:acetone (95:5). IR (ATR) 2940, 2837, 2137, 1591, 1493, 1287, 1245, 1173, 826 cm$^{-1}$. $^1$H NMR (500 MHz, Chloroform-d) δ 7.54 (d, J=8.9 Hz, 1H), 6.92 (d, J=8.8 Hz, 1H), 4.41 (s, 2H), 3.82 (s, 1H). $^{13}$C NMR (125 MHz, Chloroform-d) δ 161.04, 159.49, 136.11, 121.94, 115.21, 55.51, 46.57 (t, J=6.5 Hz). IR (ATR) 2940, 2837, 2137, 1591, 1493, 1287, 1245, 1173, 1027, 826 cm$^{-1}$.

Example 13

Preparation of (isocyanomethyl)(2-methoxyphenyl)sulfane

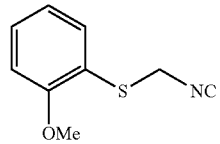

The sulfanyl formamide (11.71 g, 83%) was prepared from 2-methoxybenzenethiol (10.0 g, 71.33 mmol) based on the general formamide synthesis method (2 h at 90° C.). The formamide (2.0 g, 10.14 mmol) was dehydrated following the general method with iPr$_2$NH to provide 1.62 g (89%) as a semisolid after purification on SiO$_2$ radial chromatography (4 mm thickness rotor) using gradient (hexanes:ether 95:5 to 80:20). Semisolid.

Figure 5A:
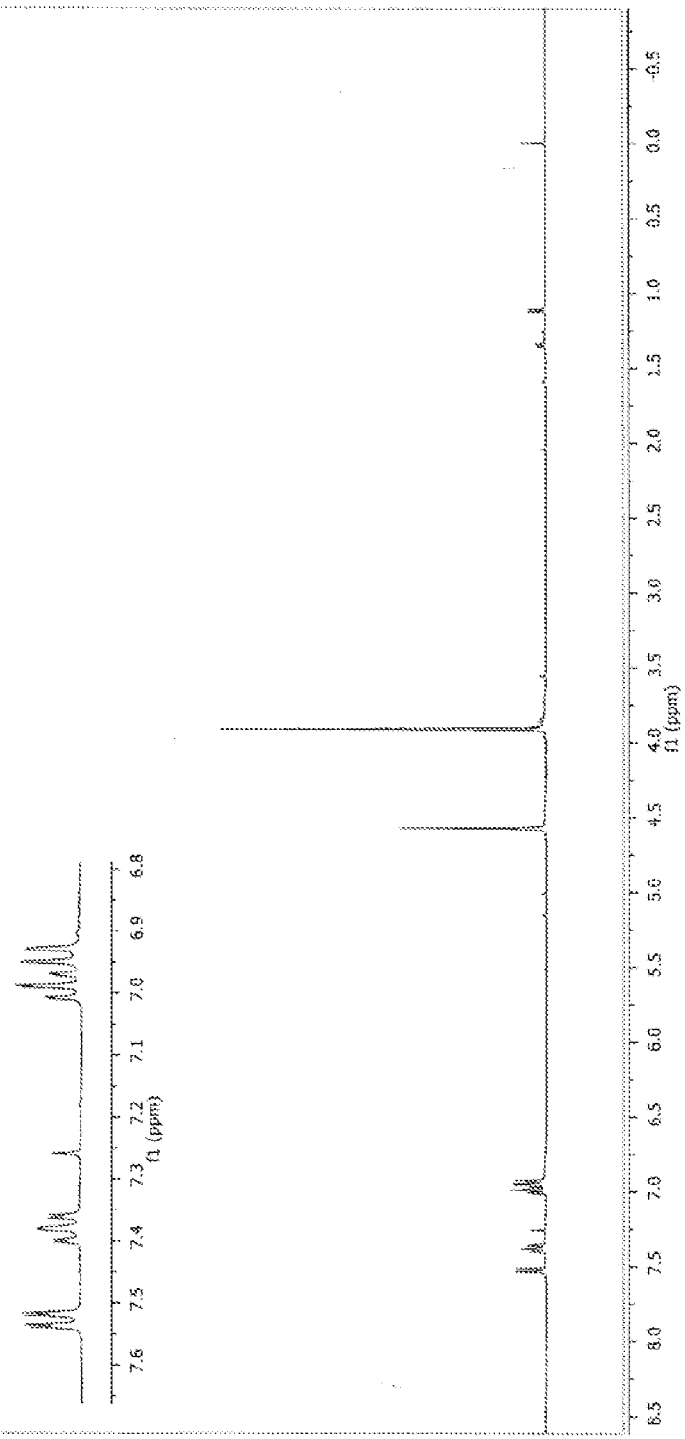
FIGS. 5A and 5B illustrate NMR data relating to the synthesis of (isocyanomethyl) (2-methoxyphenyl)sulfane, in accordance with certain embodiments of the invention.
Figure 5B:
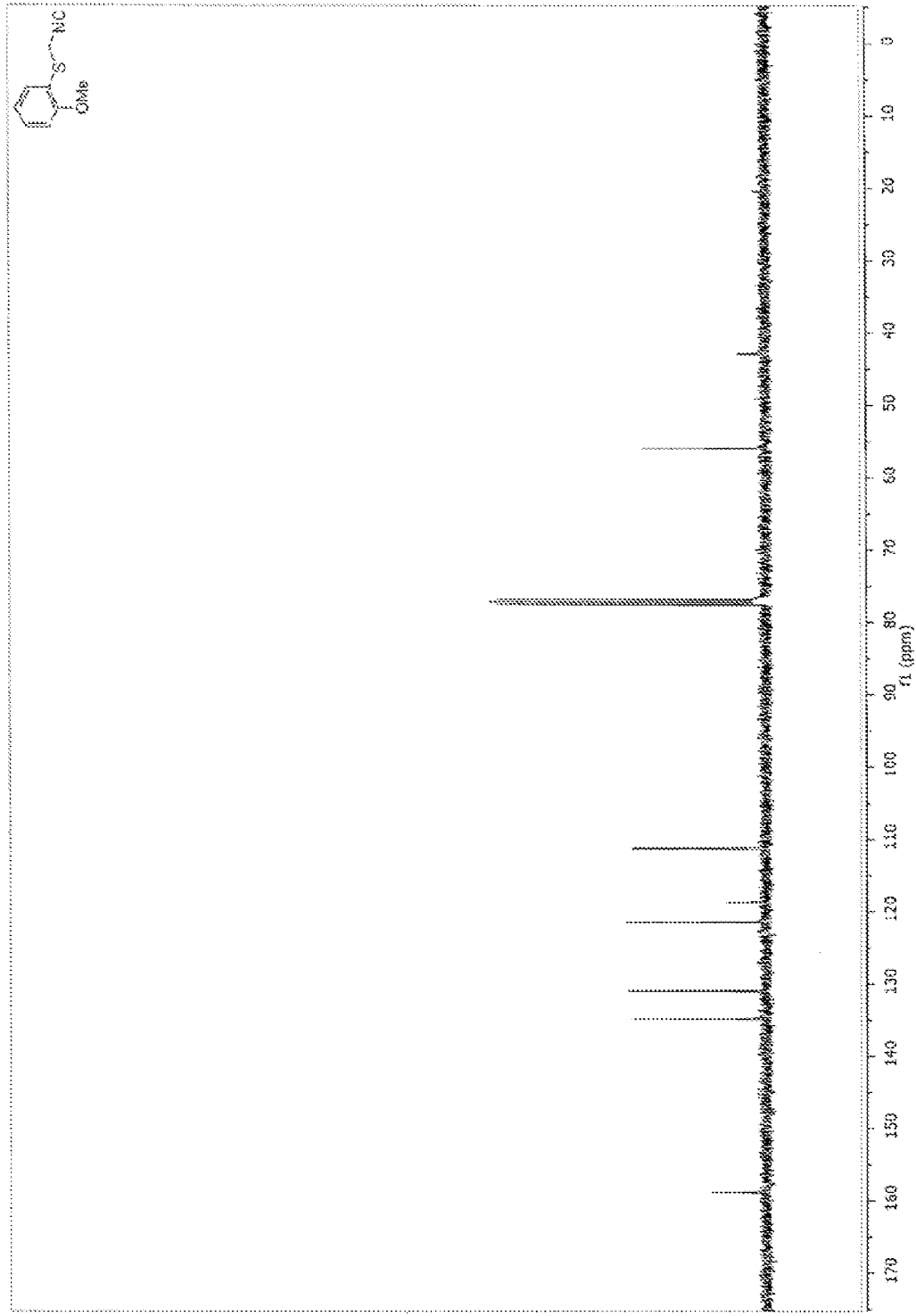

$^1$H NMR (400 MHz, Chloroform-d) δ 7.53 (dd, J=7.7, 1.7 Hz, 1H), 7.38 (ddd, J=8.1, 7.4, 1.7 Hz, 1H), 6.99 (td, J=7.6, 1.2 Hz, 1H), 6.94 (dd, J=8.3, 1.2 Hz, 1H), 4.57 (s, 2H), 3.91 (s, 3H). IR (ATR) 2940, 2838, 2137, 1581, 1478, 1432, 1273, 1243, 1021, 748 cm$^{-1}$. HRMS calculated for C$_9$H$_9$NOS 180.0478. found 180.0479 (M+H)$^+$. See FIGS. 5A and 5B.

Example 14

Preparation of (isocyanomethyl)(2-(methylthio)phenyl)sulfane

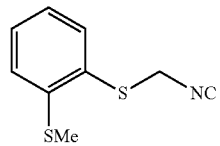

Figure 6A:
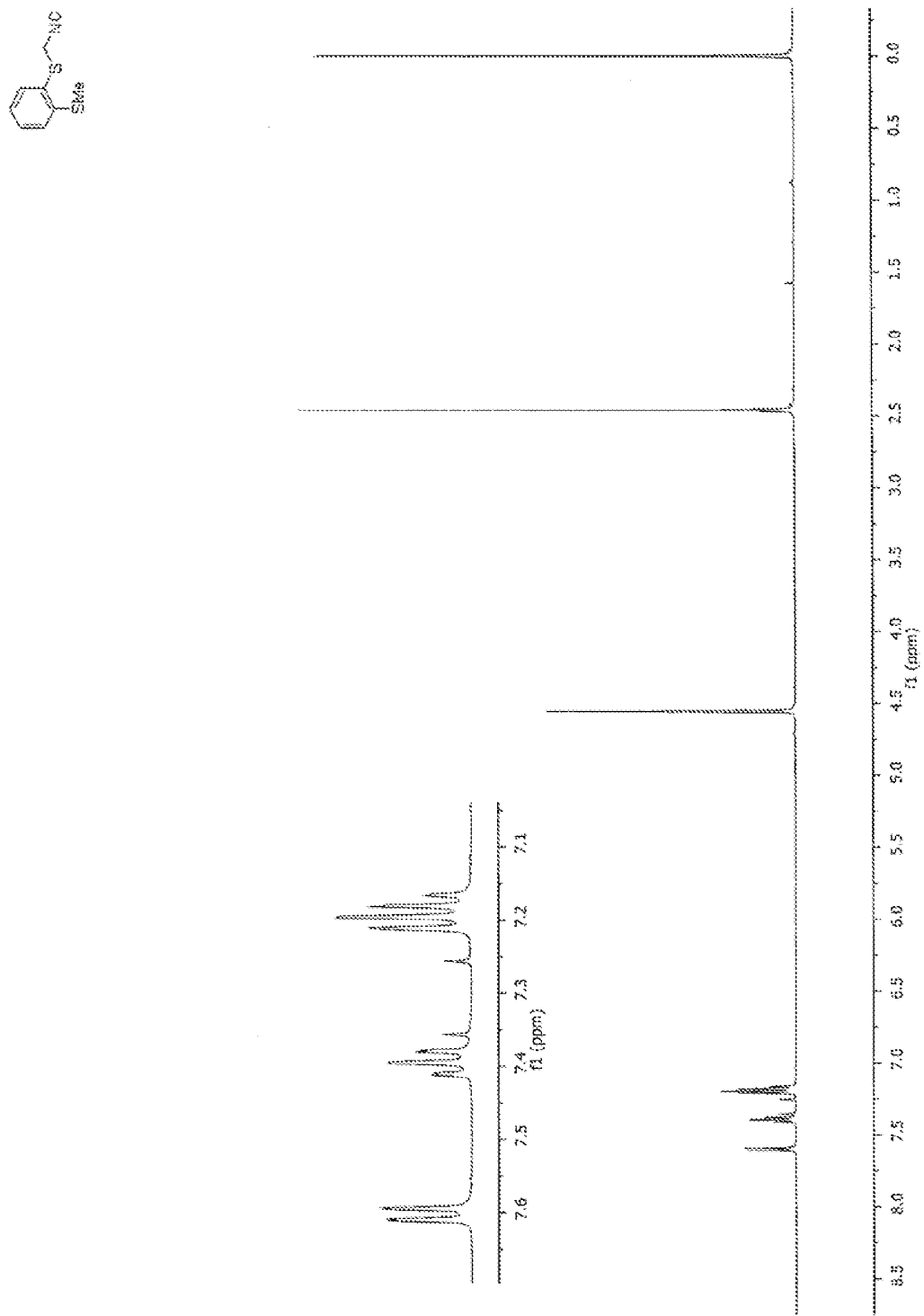
FIGS. 6A and 6B illustrate NMR data relating to the synthesis of (isocyanomethyl) (2-(methylthio)phenyl)sulfane, in accordance with certain embodiments of the invention.
Figure 6B:
Figure 6B:
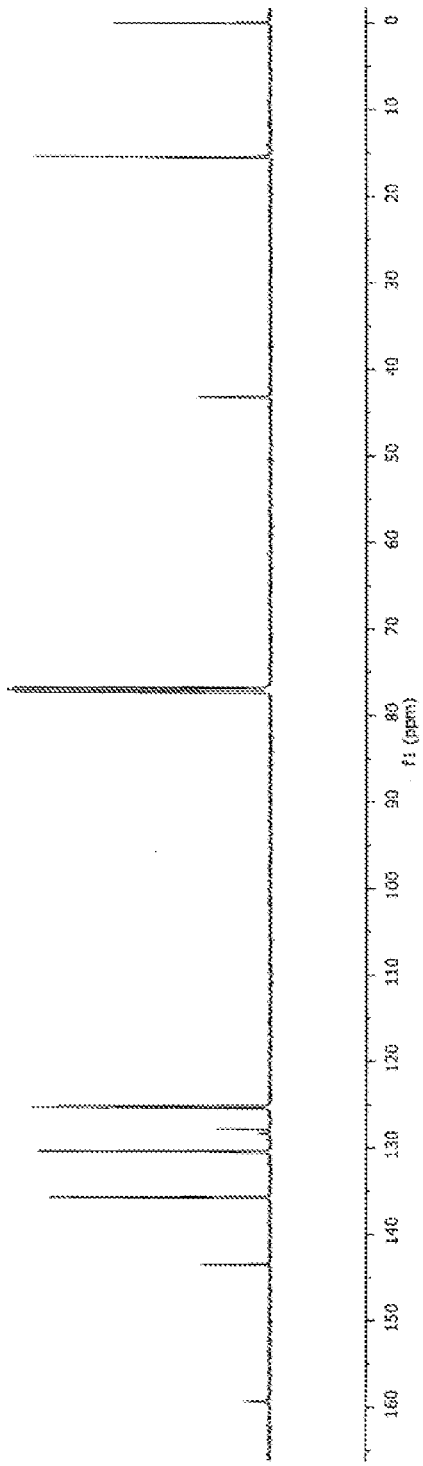

The sulfanyl formamide was prepared from 2-(methylthio)benzenethiol (1.05 g, 7.04 mmol) based on the general formamide synthesis method (2.5 h at 95° C.). The crude formamide was dehydrated following the general method with iPr$_2$NH to provide 0.52 g (67%, 2 steps) as a slightly yellow-orange solid after purification by SiO$_2$ radial chromatography (4 mm thickness rotor) using hexanes:Et$_2$O (90:10) as eluant. mp 76-77° C. $^1$H NMR (500 MHz, Chloroform-d) δ 7.60 (dd, J=7.6, 1.4 Hz, 1H), 7.40 (td, J=7.7, 1.5 Hz, 1H), 7.23-7.14 (m, 2H), 4.55 (s, 2H), 2.46 (s, 3H). $^{13}$C NMR (125 MHz, Chloroform-d) δ 159.39, 143.58, 135.75, 130.48, 127.91, 125.49, 125.25, 43.31 (t, J=6.4 Hz), 15.56. IR (ATR) 2981, 2920, 2137, 1571, 1431, 1270, 1253, 1042, 925 cm$^{-1}$. See FIGS. 6A and 6B.

Example 15

Preparation of (isocyanomethyl)(2-phenoxyphenyl)sulfane

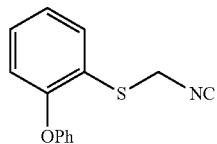

The sulfanyl formamide was prepared from 2-phenoxybenzenethiol (1.5 g, 7.42 mmol) based on the general formamide synthesis method (2.5 h at 90° C.). The crude formamide was dehydrated following the general method with iPr$_2$NH to provide 1.63 g (91%, 2 steps) as a slightly yellow oil after purification on SiO$_2$ radial chromatography (4 mm thickness rotor) using hexanes:Et$_2$O (90:10) as eluent. $^1$H NMR (400 MHz, Chloroform-d) δ 7.62 (dd, J=7.7, 1.7 Hz, 1H), 7.40-7.29 (m, 3H), 7.20-7.09 (m, 2H), 7.04-6.97 (m, 2H), 6.91 (dd, J=8.2, 1.3 Hz, 1H), 4.60 (s, 2H). $^{13}$C NMR (100 MHz, Chloroform-d) δ 159.41, 156.98, 156.58, 134.66, 130.79, 130.08, 124.36, 124.02, 122.12, 119.17, 118.84, 43.07.

Example 16

Preparation of (2,6-dimethoxyphenyl)(isocyanomethyl)sulfane

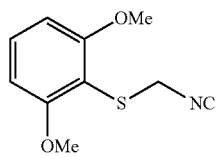

The sulfanyl formamide was prepared from 2,6-dimethoxybenzenethiol (0.65 g, 3.82 mmol) according to the general formamide synthesis method (2.5 h at 90° C.). The crude formamide was dehydrated following the general method with iPr$_2$NH to provide 520 mg (65%, 2 steps) as a white solid after purification on SiO$_2$ radial chromatography (2 mm thickness rotor) using hexanes:Et$_2$O (70:30) as eluent. mp 47-48 C. $^1$H NMR (400 MHz, Chloroform-d) δ 7.34 (t, J=8.4 Hz, 1H), 6.63 (d, J=8.4 Hz, 2H), 4.52 (s, 2H), 3.91 (s, 6H). $^{13}$C NMR (100 MHz, Chloroform-d) δ 161.21, 158.29, 131.55, 106.02, 104.47, 56.47, 42.87 (t, J=6.3 Hz). IR (ATR) 3004, 2942, 2839, 2138, 1579, 1470, 1430, 1250, 1100, 1032, 772 cm$^{-1}$; HRMS calculated for C$_{10}$H$_{11}$NO$_2$S 232.0403. found 232.0399 (M+Na)$^+$.

Example 17

Preparation of 2-((Isocyanomethyl)sulfanyl)-1-methoxy-3-(trifluoromethyl)benzene

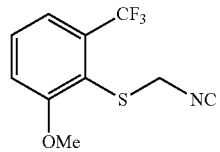

The sulfanyl formamide (1.083 g, 76%) was prepared from 2-methoxy-6-(trifluoromethyl)benzenethiol (1 g, 4.8 mmol) according to the general formamide synthesis method (2 h at 90° C.). The crude formamide (1 g, 3.36 mmol) was dehydrated following the general method with iPr$_2$NH to provide 874 mg (94%) as a white solid after purification on SiO$_2$ column chromatography, hexanes:EtOAc 80:20 to 60:40 with 1% MeOH. mp 54-55° C.; $^1$H NMR (500 MHz, Chloroform-d) δ 7.50 (t, J=8.1 Hz, 1H), 7.39 (dd, J=7.8, 1.2 Hz, 1H), 7.17 (d, J=8.6 Hz, 1H), 4.60 (s, 2H), 3.98 (s, 3H). $^{13}$C NMR (125 MHz, Chloroform-d) δ 160.91, 159.24, 135.59 (q, J=29.6 Hz), 131.31, 123.26 (q, J=274.2 Hz), 119.29 (q, J=5.8 Hz), 117.14, 114.88, 56.62, 42.82. IR (ATR) 2999, 2952, 2848, 2140, 1581, 1473, 1434, 1315, 1267, 1142, 1032, 918, 797 cm$^{-1}$; HRMS calculated for C$_{10}$H$_8$F$_3$NOS 270.0171. found 270.0169 (M+Na)$^+$.

Example 18

Preparation of (isocyanomethyl)(2-methoxynaphthalen-1-yl)sulfane

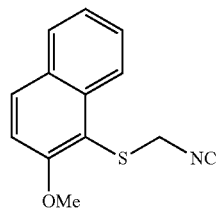

The sulfanyl formamide was prepared from 2-methoxynaphthalene-1-thiol according to the general formamide synthesis (2 h at 90° C.) The formamide (1.2 g, 4.85 mmol) was dehydrated following the general method with iPr$_2$NH to provide 0.967 g (87%, 2 steps) as a white solid after purification by SiO$_2$ flash chromatography using gradient (hexanes:EtOAc 80:20 to 60:40 with 1% MeOH). mp 99-100° C.; $^1$H NMR (400 MHz, Chloroform-d) δ 8.55 (dd, J=8.6, 1.0 Hz, 1H), 7.94 (d, J=9.1 Hz, 1H), 7.80 (d, J=8.1 Hz, 1H), 7.58 (ddd, J=8.5, 6.8, 1.4 Hz, 1H), 7.40 (ddd, J=8.1, 6.8, 1.2 Hz, 1H), 7.32 (d, J=9.1 Hz, 1H), 4.55 (s, 2H), 4.05 (s, 3H). $^{13}$C NMR (100 MHz, Chloroform-d) δ 158.90, 158.83, 136.20, 132.47, 129.49, 128.47, 128.02, 124.90, 124.34, 112.85, 111.61, 56.86, 43.54 (t, J=6.3 Hz). IR (ATR) 2941, 2481, 2138, 1505, 1263, 1246, 1067, 809 cm$^{-1}$.

Example 19

Preparation of (3,4-dimethoxyphenyl)(isocyanomethyl)sulfane

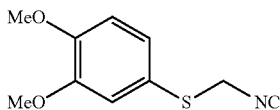

The sulfanyl formamide was prepared from 3,4-dimethoxybenzenethiol (1.5 g, 8.81 mmol) based on the general formamide synthesis method (2.5 h at 95° C.). The crude formamide was dehydrated following the general method with iPr$_2$NH to provide 0.496 g (37%) as an oil after purification on SiO$_2$ radial chromatography (4 mm thickness rotor) using gradient (hexanes:EtOAc 90:10 to 70:30). $^1$H NMR (500 MHz, Chloroform-d) δ 7.21 (dd, J=8.3, 2.1 Hz, 1H), 7.13 (d, J=2.1 Hz, 1H), 6.89 (d, J=8.3 Hz, 1H), 4.44 (s, 2H), 3.92 (s, 3H), 3.91 (s, 3H). $^{13}$C NMR (125 MHz, Chloroform-d) δ 159.66, 150.63, 149.41, 127.53, 122.24, 117.10, 111.84, 56.16, 56.07, 46.53 (t, J=6.2 Hz). IR (ATR) 2991, 2837, 2139, 1578, 1498, 1453, 1247, 1220, 1174, 1132, 1014 cm$^{-1}$.

Example 20

Preparation of (isocyanomethyl)(2,3,-dimethoxyphenyl)sulfane

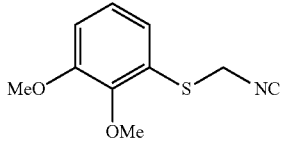

Figure 7:
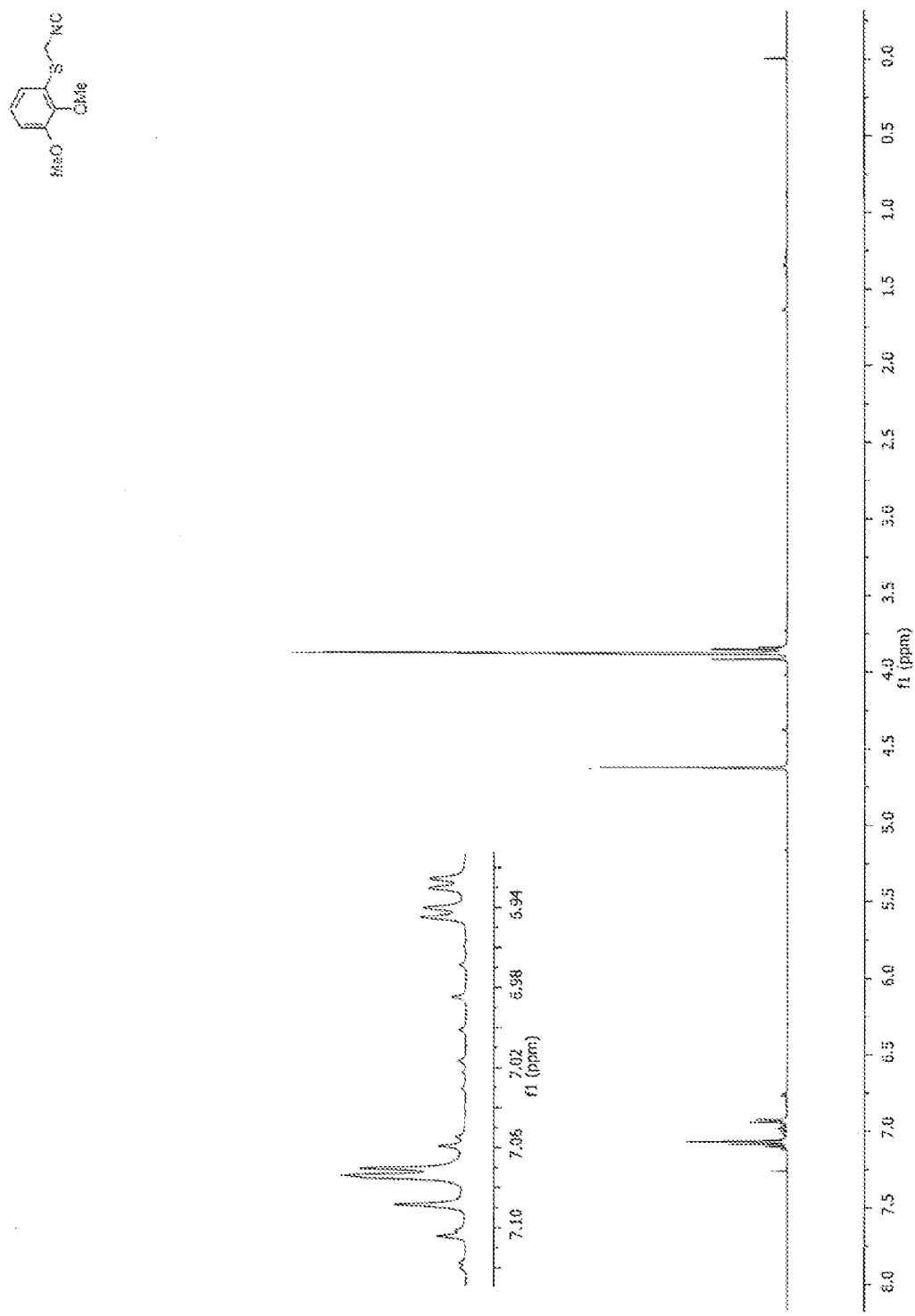
FIG. 7 illustrates NMR data relating to the synthesis of (isocyanomethyl)(2,3,-dimethoxyphenyl)sulfane, in accordance with certain embodiments of the invention.

The sulfanyl formamide was prepared from 2,3-dimethoxybenzenethiol (0.550 g, 3.23 mmol) based on the general formamide synthesis (3 h at 97° C.). The crude formamide was dehydrated following the general method with iPr$_2$NH to provide 0.254 g (38%) as an oil after purification on SiO$_2$ radial chromatography (2 mm thickness rotor) using Et$_2$O:Hexanes (60:40) as eluant. $^1$H NMR (500 MHz, Chloroform-d) δ 7.12-7.05 (m, 2H), 6.94 (dd, J=7.3, 2.4 Hz, 1H), 4.63 (s, 2H), 3.89 (s, 3H), 3.88 (s, 3H). It was believed that the quality of the thiol contributed to the low yield. See FIG. 7.

Example 21

Preparation of (isocyanomethyl)(2,3,4-trimethoxyphenyl)sulfane

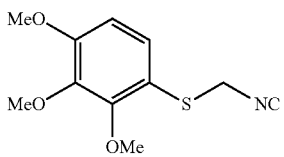

Figure 8A:
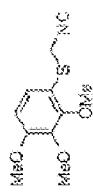
FIGS. 8A and 8B illustrate NMR data relating to the synthesis of (isocyanomethyl) (2,3,4-trimethoxyphenyl)sulfane, in accordance with certain embodiments of the invention.
Figure 8A:
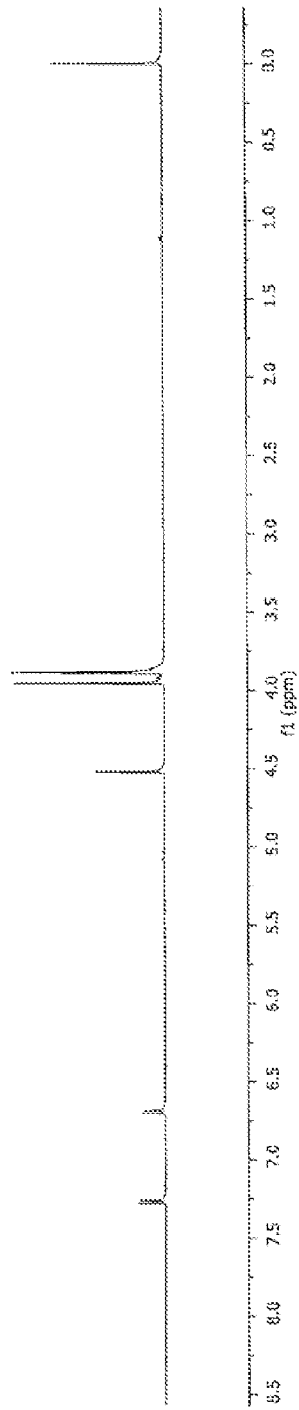
Figure 8B:
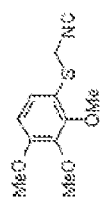
Figure 8B:
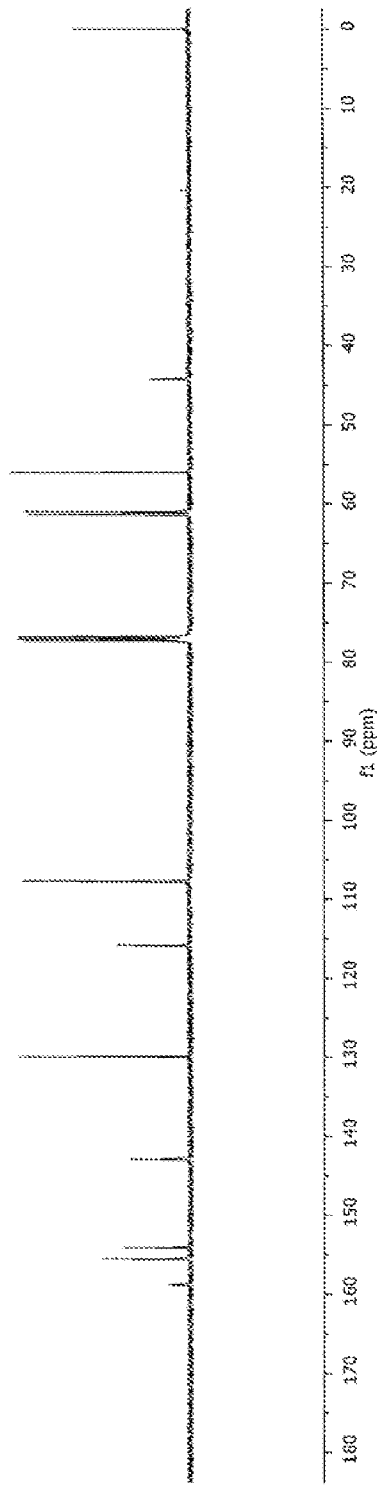

The sulfanyl formamide was prepared from 2,3,4-trimethoxybenzenethiol (0.85 g, 42.45 mmol) based on the general formamide method (2.5 h at 95° C.). The crude formamide was dehydrated following the general method with iPr$_2$NH to provide 0.603 g (59%) as a slightly yellow oil after purification on SiO$_2$ radial chromatography (2 mm thickness rotor) using hexanes:Et$_2$O (70:30) as eluant. $^1$H NMR (500 MHz, Chloroform-d) δ 7.27 (d, J=8.7 Hz, 1H), 6.69 (d, J=8.7 Hz, 1H), 4.52 (s, 2H), 3.95 (s, 3H), 3.89 (s, 3H), 3.88 (s, 3H). $^{13}$C NMR (125 MHz, Chloroform-d) δ 158.81, 155.57, 154.16, 142.89, 130.02, 115.85, 107.78, 61.41, 61.03, 56.11, 44.31. IR (ATR) 2939, 2839, 2137, 1579, 1481, 1406, 1089, 1009, 798 cm$^{-1}$. See FIGS. 8A and 8B.

Example 22

Preparation of 2-((1-isocyanocyclohexyl)thio)pyridine

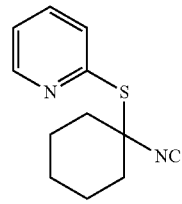

The product was prepared from 2-((isocyanomethyl)thio)pyridine (0.08 g, 0.53 mmol) according to the general alkylation procedure (7 h @ 7° C.) to provide 52 mg (45%) as an oil after purification by DIOL column chromatography using gradient (hexanes:EtOAc 99:1 to 98:2). $^1$H NMR (400 MHz, Chloroform-d) δ 8.62 (dd, J=4.8, 1.9 Hz, 1H), 7.70 (td, J=7.6, 2.0 Hz, 1H), 7.64 (d, J=7.7 Hz, 1H), 7.32-7.22 (m, 1H), 2.22 (d, J=13.2 Hz, 2H), 1.97-1.84 (m, 2H), 1.81-1.59 (m, 5H), 1.41-1.27 (m, 1H). $^{13}$C NMR (100 MHz, Chloroform-d) δ 157.19 (t, J=4 Hz), 153.54, 150.38, 137.22, 129.78, 123.29, 68.1 (t, J=5.4 Hz), 38.56, 24.69, 22.29.

Example 23

General Alkylation Method

Neat mono or dihalide (2 eq or 1 eq) and the arylsulfanyl methyl isonitrile (1 eq) were sequentially added to a cold (0° C.) suspension of sodium hydride (5 eq) in dimethylformamide (0.15 M in regard to arylsulfanylisonitrile). After stirring at 5° C. for 24 h, the mixture was diluted with a 50:50 mixture of ice and brine. The mixture was extracted with ethyl acetate (×4), the combined organic extract was washed with brine, dried (Na$_2$SO$_4$), and concentrated to afford the crude isonitrile. The crude isonitrile was filtered through a SiO$_2$ plug (10×50 mm) and then purified by SiO$_2$ flash chromatography or SiO$_2$ radial chromatography to afford the pure isonitrile.

Example 24

Preparation of (1-isocyanocyclohexyl)(naphthalen-2-yl)sulfane

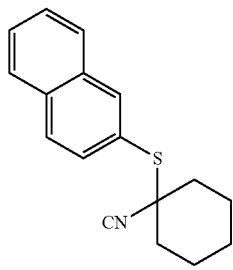

The product was prepared from (isocyanomethyl)(naphthalen-2-yl)sulfane (0.4 g, 2.01 mmol) according to the general alkylation procedure (45 h at room temperature) to provide 437 mg of (81%) as an oil after purification by SiO$_2$ radial chromatography (4 mm) using gradient (hexanes: acetone 90:10 to 80:20). IR (ATR) 2939, 286, 2121, 1450, 905, 727 cm$^{-1}$. $^1$H NMR (500 MHz, Chloroform-d) δ 8.18 (s, 1H), 7.91-7.81 (m, 3H), 7.69 (dd, J=8.5, 1.7 Hz, 1H), 7.57-7.48 (m, 2H), 1.99 (d, J=13.3 Hz, 2H), 1.81-1.65 (m, 4H), 1.67-1.52 (m, 3H), 1.35-1.23 (m, 1H). $^{13}$C NMR (125 MHz, Chloroform-d) δ 157.20, 137.41, 133.81, 133.52, 133.16, 128.67, 128.28, 127.79, 127.46, 126.71, 126.23, 68.06, 38.18, 24.75, 22.28.

Example 25

Preparation of (1-isocyanocyclohexyl)(4-methoxyphenyl)sulfane

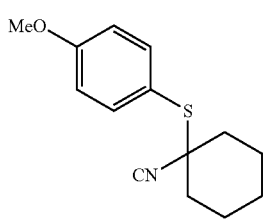

The product was prepared from (isocyanomethyl)(4-methoxyphenyl)sulfane (0.45 g, 2.79 mmol) according to the general alkylation procedure (29 h at room temperature) to provide 457 mg (74%) as a colorless oil after purification by SiO$_2$ radial chromatography (4 mm) using hexanes:Et$_2$O (80:20). IR (ATR) 2937, 2860, 2119, 1591, 1493, 1246, 1172, 1028, 828 cm$^{-1}$. $^1$H NMR (500 MHz, Chloroform-d) δ 7.56 (d, J=8.7 Hz, 2H), 6.92 (d, J=8.7 Hz, 2H), 3.82 (s, 3H), 2.00-1.91 (m, 2H), 1.75-1.51 (m, 7H), 1.36-1.24 (m, 1H). $^{13}$C NMR (125 MHz, Chloroform-d) δ 161.42, 156.65, 138.77, 119.67, 114.68, 67.97 (t, J=5.3 Hz), 55.45, 37.92, 24.79, 22.28.

Example 26

Preparation of (1-isocyanocyclohexyl)(2-methoxyphenyl)sulfane

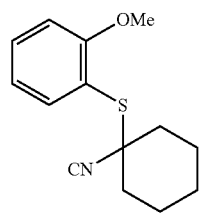

The product was prepared from (isocyanomethyl)(2-methoxyphenyl)sulfane (1 g, 5.58 mmol) according to the general alkylation procedure (32 h at room temperature) to provide 987 mg (72%) as a semisolid after purification by SiO$_2$ radial chromatography (4 mm rotor) using gradient (hexanes:Et$_2$O 90:10 to 70:30 with 1% MeOH). $^1$H NMR (400 MHz, Chloroform-d) δ 7.67 (dd, J=7.5, 1.8 Hz, 1H), 7.43 (ddd, J=8.4, 7.5, 1.8 Hz, 1H), 6.99 (td, J=7.5, 1.3 Hz, 1H), 6.96 (dd, J=8.3, 1.2 Hz, 1H), 3.87 (s, 3H), 1.97 (d, J=13.1, Hz, 2H), 1.82-1.49 (m, 7H), 1.35-1.21 (m, 1H). $^{13}$C NMR (100 MHz, Chloroform-d) δ 161.21, 156.52, 139.87, 132.25, 121.09, 116.69, 111.27, 68.38 (t, J=5.3 Hz), 55.84, 38.01, 24.68, 22.31. IR (ATR) 2937, 2860, 2120, 1583, 14775, 1431, 1273, 1246, 1024, 752 cm$^{-1}$. HRMS calculated for C$_{14}$H$_{17}$NOS 270.0923. found 270.0916 (M+Na).

Example 27

Preparation of (1-isocyanocyclohexyl)(2-(methylthio)phenyl)sulfane

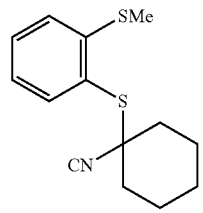

The product was prepared from (isocyanomethyl)(2-(methylthio)phenyl)sulfane (0.5 g, 2.56 mmol) according to the general alkylation procedure (65 h at 5° C.) to provide 445 mg (66%) as a white solid after purification by SiO$_2$ radial chromatography (4 mm rotor) using hexanes:Et$_2$O (90:10) as eluent. Mp 58-59° C. $^1$H NMR (500 MHz, Chloroform-d) δ 7.73 (dd, J=7.9, 1.5 Hz, 1H), 7.44-7.38 (m, 1H), 7.20-7.13 (m, 2H), 2.43 (s, 3H), 2.01 (d, J=13.9 Hz, 1H), 1.88-1.80 (m, 2H), 1.75-1.53 (m, 5H), 1.32-1.21 (m, 1H). $^{13}$C NMR (125 MHz, Chloroform-d) δ 157.58, 147.19, 138.40, 130.90, 126.20, 124.77, 124.13, 69.2 (t, J=5.3 Hz), 38.09, 24.65, 22.40, 15.57. IR (ATR) 2981, 2920, 2137, 1571, 1431, 1042, 748 cm$^{-1}$. IR (ATR) 3054, 2937, 2860, 2119, 1571, 1448, 1431, 1013, 749 cm$^{-1}$.

Example 28

Preparation of (1-isocyanocyclohexyl)(2-phenoxyphenyl)sulfane

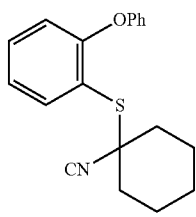

The product was prepared from (isocyanomethyl)(2-phenoxyphenyl)sulfane (0.9 g, 3.73 mmol) according to the general alkylation procedure (45 h at room temperature) to provide 837 mg (73%) as a white solid after purification by $SiO_2$ radial chromatography (4 mm) using hexanes:acetone 90:10. mp 76-76.5° C. $^1$H NMR (500 MHz, Chloroform-d) δ 7.81 (dd, J=7.7, 1.8 Hz, 1H), 7.41-7.32 (m, 3H), 7.18-7.10 (m, 2H), 7.02-6.95 (m, 2H), 6.92 (dd, J=8.2, 1.4 Hz, 1H), 2.05 (dt, J=13.2, 3.9 Hz, 2H), 1.88-1.79 (m, 2H), 1.76-1.69 (m, 2H), 1.67-1.54 (m, 4H), 1.35-1.24 (m, 1H). $^{13}$C NMR (125 MHz, Chloroform-d) δ 159.54, 157.07, 156.82, 140.03, 132.17, 129.99, 123.91, 123.81, 119.86, 119.15, 118.63, 68.73 (t, J=5.1 Hz), 38.28, 24.72, 22.39. IR (ATR) 2937, 2860, 2120, 1593, 1492, 1467, 1439, 1233 cm$^{-1}$.

Example 29

Preparation of (1-isocyanocyclohexyl)(2-methoxy-6-(trifluoromethyl)phenyl)sulfane

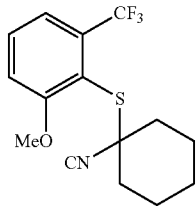

The product was prepared from 2-((isocyanomethyl)sulfanyl)-1-methoxy-3-(trifluoromethyl)benzene (0.36 g, 1.46 mmol) according to the general alkylation procedure (30 h at 5° C.) to provide 500 mg (78%) as a white solid after purification by $SiO_2$ radial chromatography (eluent). mp 81-82° C. $^1$H NMR (500 MHz, Chloroform-d) δ 7.49 (t, J=8.0 Hz, 1H), 7.38 (dd, J=7.9, 1.2 Hz, 1H), 7.15 (d, J=8.3 Hz, 1H), 3.96 (s, 3H), 2.00 (d, J=12.4 Hz, 2H), 1.79-1.58 (m, 7H), 1.30-1.17 (m, 1H). $^{13}$C NMR (125 MHz, Chloroform-d) δ 162.22, 156.92, 136.47 (q, J=28.7 Hz), 131.57, 123.32 (q, J=274.3 Hz), 119.11 (q, J=6.0 Hz), 117.21, 114.58, 67.95 (t, J=5.3 Hz), 56.08, 39.10, 24.56, 22.59. IR (ATR) 2935, 2862, 2122, 1579, 1310, 1272, 1128, 1033, 796 cm$^{-1}$. HRMS calculated for $C_{15}H_{19}NO_4S$ 338.0797. found 338.0799 (M+Na)$^+$.

Example 30

Preparation of 3,4-dimethoxyphenyl)(1-isocyanocyclohexyl)sulfane

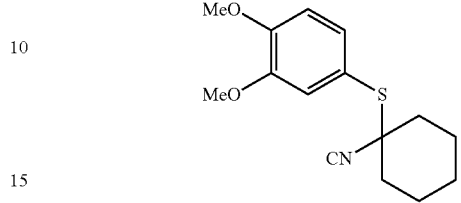

The product was prepared from (3,4-dimethoxyphenyl)(isocyanomethyl)sulfane (0.35 g, 1.67 mmol) according to the general alkylation procedure (22 h at room temperature) to provide 354 mg (76%) as a colorless oil after purification by $SiO_2$ radial chromatography (4 mm) using gradient (hexanes:EtOAc 90:10 to 70:30). $^1$H NMR (400 MHz, Chloroform-d) δ 7.24-7.16 (m, 2H), 6.88 (d, J=8.1 Hz, 1H), 3.92 (s, 3H), 3.91 (s, 3H), 2.04-1.87 (m, 2H), 1.79-1.50 (m, 7H), 1.39-1.22 (m, 1H). $^{13}$C NMR (100 MHz, Chloroform-d) δ 156.83, 150.92, 148.88, 130.32, 119.80, 119.53, 111.20, 67.98 (t=5 Hz), 56.12, 55.96, 37.87, 24.74, 22.23. IR (ATR) 2937, 2860, 2119, 1591, 1493, 1246, 1172, 1028, 828 cm$^{-1}$.

Example 31

Preparation of (2,3-dimethoxyphenyl)(1-isocyanocyclohexyl)sulfane

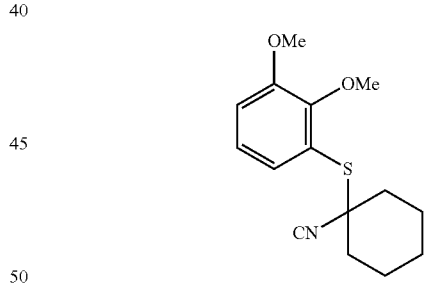

The product was prepared from (2,4-dimethoxyphenyl)(isocyanomethyl)sulfane (0.23 g, 1.10 mmol) according to the general alkylation procedure (48 h at 7° C.) to provide 239 mg (78%) as an oil after purification by $SiO_2$ radial chromatography (1 mm) using gradient (hexanes:acetone 95:5 to 90:10). $^1$H NMR (400 MHz, Chloroform-d) δ 7.31 (s, 1H), 7.10 (t, J=8.0 Hz, 1H), 7.02 (dd, J=8.3, 1.6 Hz, 1H), 3.88 (s, 3H), 3.86 (s, 3H), 2.00 (d, J=13.6 Hz, 2H), 1.87-1.73 (m, 2H), 1.75-1.66 (m, 2H), 1.67-1.54 (m, 3H), 1.34-1.22 (m, 1H). $^{13}$C NMR (100 MHz, Chloroform-d) δ 156.77, 153.26, 151.54, 130.15, 124.31, 123.38, 114.67, 68.51 (t, J=5.3 Hz), 61.44, 56.01, 38.17, 24.65, 22.32. IR (ATR) 2937, 2860, 2120, 1469, 1420, 1260, 1231, 1044, 1003, 781, 745 cm$^{-1}$.

Example 32

Preparation of (1-isocyanocyclohexyl)(2,3,4-trimethoxyphenyl)sulfane

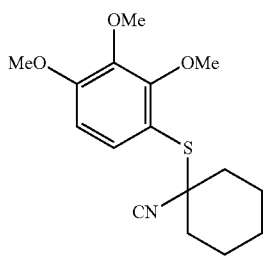

The product was prepared from (isocyanomethyl)(2,3,4-trimethoxyphenyl)sulfane (0.35 g, 5.58 mmol) according to the general alkylation procedure (40 h at 5° C.) to provide 315 mg (70%) as a white solid after purification by $SiO_2$ radial chromatography (1 mm rotor) using hexanes:$Et_2O$ (70:30) as eluent. $^1$H NMR (500 MHz, Chloroform-d) δ 7.42 (d, J=8.7 Hz, 1H), 6.72 (d, J=8.7 Hz, 1H), 3.93 (s, 3H), 3.89 (s, 3H), 3.88 (s, 3H), 1.97 (d, J=13.3 Hz, 2H), 1.83-1.69 (m, 4H), 1.68-1.52 (m, 3H), 1.34-1.21 (m, 1H). $^{13}$C NMR (125 MHz, Chloroform-d) δ 156.50, 156.36, 156.20, 142.58, 134.26, 114.06, 107.52, 68.72 (t, J=5.1 Hz), 61.80, 61.05, 56.08, 38.06, 24.72, 22.39.

Example 33

Preparation of (2-isocyano-1,3-diphenylpropan-2-yl)(2-methoxyphenyl)sulfane

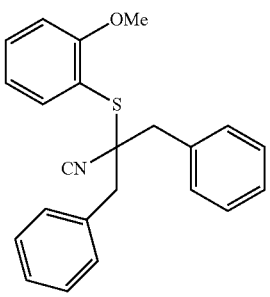

The product was prepared from (isocyanomethyl)(2-methoxyphenyl)sulfane (0.1 g, 5.58 mmol) according to the general alkylation procedure (16 h at 5° C.) to provide 110 mg (55%) as an oil after purification by $SiO_2$ radial chromatography (1 mm rotor) using gradient (hexanes:$Et_2O$:DCM 90:5:5 to 80:10:10). $^1$H NMR (500 MHz, Chloroform-d) δ 7.56 (d, J=7.6 Hz, 1H), 7.43 (t, J=7.8 Hz, 1H), 7.31 (s, 10H), 7.00-6.93 (m, 2H), 3.86 (s, 3H), 3.14 (d, J=13.8 Hz, 2H), 3.02 (d, J=13.9 Hz, 2H).

Example 34

Preparation of (1-isocyanocyclopentyl)(2-methoxyphenyl)sulfane

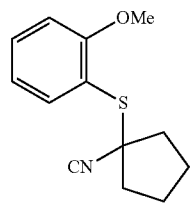

The product was prepared from (isocyanomethyl)(2-methoxyphenyl)sulfane (0.1 g, 5.58 mmol) according to the general alkylation procedure (23 h at 7° C.). Crude $^1$H NMR (500 MHz, Chloroform-d) δ 7.67 (dd, J=7.6, 1.8 Hz, 1H), 7.42 (ddd, J=8.0, 7.5, 1.8 Hz, 1H), 7.00 (td, J=7.6, 1.2 Hz, 1H), 6.96 (dd, J=8.3, 1.2 Hz, 1H), 3.89 (s, 3H), 2.18-2.08 (m, 4H), 1.95-1.83 (m, 4H).

Example 35

Preparation of (4-isocyanoheptan-4-yl)(2-methoxyphenyl)sulfane

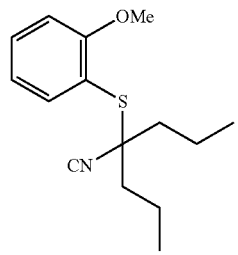

The product was prepared from (isocyanomethyl)(2-methoxyphenyl)sulfane (0.1 g, 5.58 mmol) according to the general alkylation procedure (16 h at 5° C.). Compound not isolated.

Example 36

Preparation of 2-((1-isocyano-1-phenylethyl)thio)pyridine

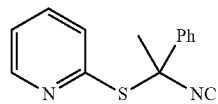

To a cold (−78° C.) solution of (S)-(−)-α-methylbenzyl isocyanide (0.1 g, 0.76 mmol) in dry THF (7.6 mL), a BuLi solution in hexanes (0.3 mL, 0.8 mmol) was added dropwise. After 10 min at the same temperature, a solution of diphenyl disulfide (168 mg, 0.76 mmol) in dry THF (1 mL) was added in one portion. After 10 min, the reaction was diluted with cold half-saturated $NH_4Cl$ solution (10 mL), and the mixture was extracted with EtOAc (×3). 77 mg (66%) were obtained as an oil after purification on DIOL column using hexanes:EtOAc (90:10) as eluent. $^1$H NMR (400 MHz, Chloroform-d) δ 8.54 (ddd, J=4.9, 2.0, 0.9 Hz, 1H), 7.66-7.57 (m, 3H), 7.43-7.30 (m, 4H), 7.20 (ddd, J=7.6, 4.8, 1.2 Hz, 1H), 2.18 (s, 3H). $^{13}$C NMR (125 MHz, Chloroform-d) δ 159.47, 154.22, 150.26, 138.57, 137.05, 128.79, 128.76, 128.72, 125.30, 123.15, 69.70, 32.22. IR (ATR) 3063, 2121, 1572, 1448, 1418, 1117, 1075, 756, 694 cm$^-$.

Example 37

Exchange

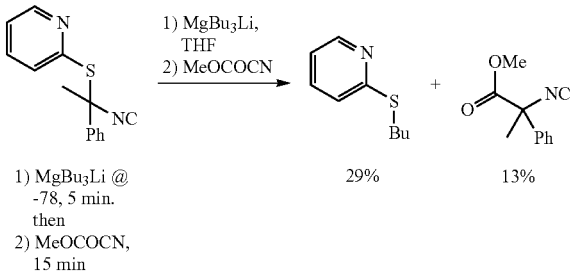

| | | |
|---|---|---|
| 1) MgBu₃Li @ -78, 5 min. then | 29% | 13% |
| 2) MeOCOCN, 15 min | | |

A cold solution (−78° C.) of 2-((1-isocyano-1-phenyl-ethyl)thio)pyridine (30 mg, 0.124 mmol) in THF (4 mL) was treated with a MgBu₃Li solution (1.05 eq) at the same temperature. The MgBu₃Li solution was prepared from dibutylmagnesium solution in heptanes (260 μL, 0.5 M) and BuLi solution in hexanes (49 μL) at −78° C. After 5 min, methyl cyanoformate (1.0 eq) was added in one portion. The reaction was diluted after 15 min with ice water, and extracted with EtOAc (×3). The crude was purified by SiO₂ radial chromatography (1 mm) to yield the isonitrile (3 mg, 13%) and the thioether (6 mg, 29%).

Methyl 2-isocyano-2-phenylpropanoate: $^1$H NMR (400 MHz, Chloroform-d) δ 7.57-7.52 (m, 2H), 7.46-7.35 (m, 3H), 3.79 (s, 3H), 2.03 (s, 3H). $^{13}$C NMR (100 MHz, Chloroform-d) δ 168.84, 160.15, 136.59, 131.03, 129.11, 124.95, 77.36, 54.08, 28.02. IR (ATR) 2957, 2925, 2138, 1748, 1448, 1255, 1117 cm$^{-1}$.

2-(Butylthio)pyridine: $^1$H NMR (400 MHz, Chloroform-d) δ 8.42 (ddd, J=5.0, 1.9, 1.0 Hz, 1H), 7.46 (ddd, J=8.1, 7.3, 1.9 Hz, 1H), 7.16 (dt, J=8.0, 1.0 Hz, 1H), 6.96 (ddd, J=7.4, 4.9, 1.1 Hz, 1H), 3.16 (dd, J=7.9, 6.9 Hz, 2H), 1.69 (p, J=7.3 Hz, 3H), 1.48 (dq, J=13.9, 7.1, 6.7 Hz, 3H), 0.94 (t, J=7.3 Hz, 3H).

Example 38

Exchange

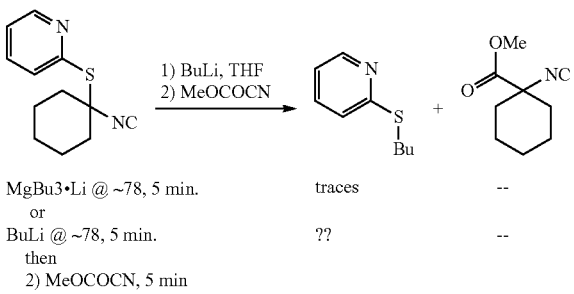

| | | |
|---|---|---|
| MgBu3•Li @ ~78, 5 min. or | traces | -- |
| BuLi @ ~78, 5 min. then 2) MeOCOCN, 5 min | ?? | -- |

The magnesiate gave only a trace of exchange product (small reporter signal at 3.16 ppm). BuLi appeared to have worked, but the product did not correspond with that obtained using the o-methoxy substrate.

Example 39

Exchange

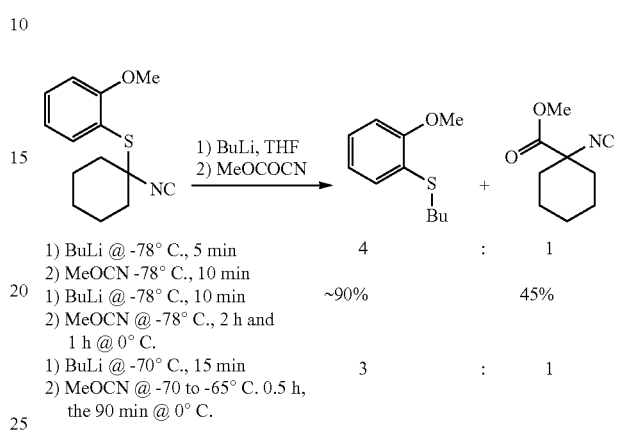

| | | |
|---|---|---|
| 1) BuLi @ -78° C., 5 min | 4 | 1 |
| 2) MeOCN -78° C., 10 min | | |
| 1) BuLi @ -78° C., 10 min | ~90% | 45% |
| 2) MeOCN @ -78° C., 2 h and 1 h @ 0° C. | | |
| 1) BuLi @ -70° C., 15 min | 3 | 1 |
| 2) MeOCN @ -70 to -65° C. 0.5 h, the 90 min @ 0° C. | | |

A cold solution (−78° C.) of (1-isocyanocyclohexyl)(2-methoxyphenyl)sulfane (50 mg, 0.2 mmol) in THF (6.7 mL) was treated with a BuLi solution in hexanes (140 μL, 1.05 eq) at the same temperature. After 10 min, methyl cyanoformate (1.5 eq) was added in one portion. After 2 h, the reaction was diluted with ice water, and extracted with EtOAc (×3). The crude was purified by SiO2 radial chromatography (1 mm) using gradient (hexane:Et2O 95:5 to 90:10) to yield the isonitrile (15 mg, 45%) and the thioether.

Methyl 1-isocyanocyclohexane-1-carboxylate: 1H NMR (500 MHz, Chloroform-d) δ 3.82 (s, 3H), 2.00 (d, J=12.7 Hz, 2H), 1.87-1.79 (m, 2H), 1.76-1.64 (m, 5H), 1.34-1.21 (m, 1H).

Butyl(2-methoxyphenyl)sulfane: 1H NMR (500 MHz, Chloroform-d) δ 7.25 (dd, J=7.7, 1.7 Hz, 1H), 7.16 (ddd, J=8.1, 7.5, 1.6 Hz, 1H), 6.92 (td, J=7.6, 1.2 Hz, 1H), 6.84 (dd, J=8.2, 1.2 Hz, 1H), 3.89 (s, 3H), 2.89 (dd, J=7.3, 7.5 Hz, 2H), 1.68-1.60 (m, 2H), 1.47 (dp, J=8.9, 7.4 Hz, 2H), 0.92 (t, J=7.4 Hz, 3H).

Example 40

Exchange

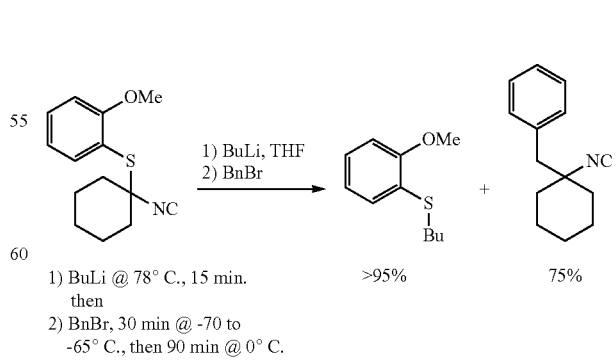

| | | |
|---|---|---|
| 1) BuLi @ 78° C., 15 min. then | >95% | 75% |
| 2) BnBr, 30 min @ -70 to -65° C., then 90 min @ 0° C. | | |

A cold solution (−78° C.) of (1-isocyanocyclohexyl)(2-methoxyphenyl)sulfane (63 mg, 0.25 mmol) in THF (5.1 mL) was treated with a BuLi solution in hexanes (170 µL, 1.05 eq) at the same temperature. After 15 min, benzyl bromide (1.2 eq) was added in one portion. The reaction was stirred for 30 min with a gradual increase of temperature (−70 to −65° C.), and then was stirred for 90 min at 0° C. The reaction was diluted with ice water, and extracted with EtOAc (×3). The crude was purified by SiO2 radial chromatography (1 mm) using hexane:EtOAc:DCM (90:5:5) as eluent to yield the isonitrile (38 mg, 75%) and the thioether. (>90%, NMR).

((1-isocyanocyclohexyl)methyl)benzene: $^1$H NMR (400 MHz, Chloroform-d) δ 7.36-7.24 (m, 5H), 2.85 (dd, J=2.0, 1.9 Hz), 1.81 (d, J=12.5 Hz, 2H), 1.74-1.59 (m, 5H), 1.43-1.30 (m, 2H), 1.22-1.05 (m, 1H).

Example 41

Exchange

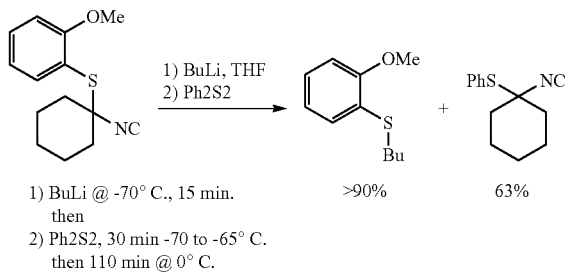

1) BuLi @ −70° C., 15 min. then
2) Ph2S2, 30 min −70 to −65° C. then 110 min @ 0° C.

>90%    63%

A cold solution (−70° C.) of (1-isocyanocyclohexyl)(2-methoxyphenyl)sulfane (65 mg, 0.26 mmol) in THF (5.3 mL) was treated with a BuLi solution in hexanes (170 µL, 1.05 eq) at the same temperature. After 15 min, neat diphenyl disulfide (1.2 eq) was added in one portion under a nitrogen blanket. The reaction was stirred for 30 min with a gradual increase of temperature (−70 to −65° C.), and then was stirred for 110 min at 0° C. The reaction was diluted with ice water, and extracted with EtOAc (×3). The crude was purified by SiO$_2$ radial chromatography (1 mm) using hexane:EtOAc (95:5) as eluent to yield the isonitrile (36 mg, 63%, NMR) and the thioether (>95%, NMR).

Example 42

Exchange

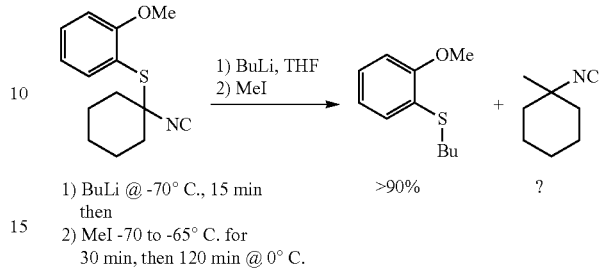

1) BuLi @ −70° C., 15 min then
2) MeI −70 to −65° C. for 30 min, then 120 min @ 0° C.

>90%    ?

A cold solution (−70° C.) of (1-isocyanocyclohexyl)(2-methoxyphenyl)sulfane (51 mg, 0.21 mmol) in THF (4.1 mL) was treated with a BuLi solution in hexanes (140 µL, 1.05 eq) at the same temperature. After 15 min, methyl iodide (1.2 eq) was added in one portion. The reaction was stirred for 30 min with a gradual increase of temperature (−70 to −65° C.), and then was stirred for 110 min at 0° C. The reaction was diluted with ice water, and extracted with EtOAc (×3). The product could not be located in the crude.

Example 43

Exchange

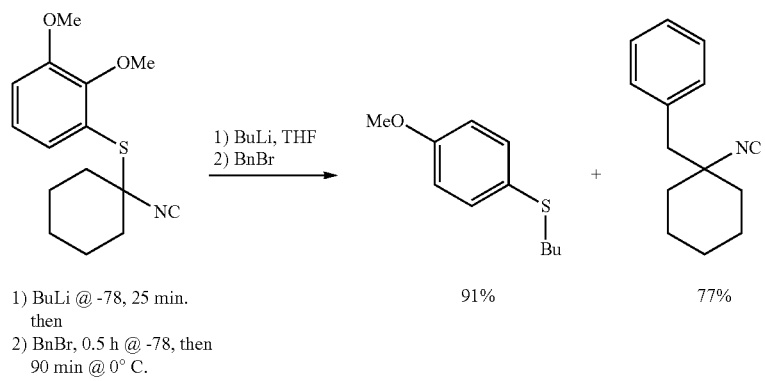

1) BuLi @ −78, 25 min. then
2) BnBr, 0.5 h @ −78, then 90 min @ 0° C.

91%    77%    (NMR, Exp #711)

A cold solution (−78° C.) of (1-isocyanocyclohexyl)(2,3-dimethoxyphenyl)sulfane (60 mg, 0.22 mmol) in THF (4.3 mL) was treated with a BuLi solution in hexanes (140 µL, 1.05 eq) at the same temperature. After 15 min, benzyl bromide (1.2 eq) was added in one portion. The reaction was stirred for 30 min at −78° C. and then was stirred for 90 min at 0° C. The reaction was diluted with ice water, and extracted with EtOAc (×3). After filtration on a SiO$_2$ plug using 70:30 hexane:Et2O, 80 mg of material were obtained corresponding to the isonitrile (77%) and the thioether (91%).

The results demonstrated that even with the presence of an additional methoxy group, the chelation effect predominates for the promotion of the exchange.

Example 44

Exchange

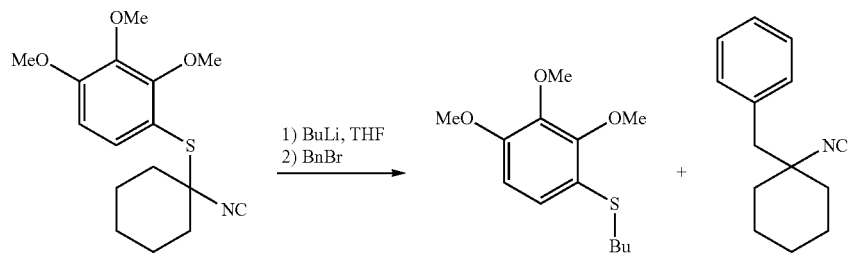

1) BuLi @ -78, 15 min.
then
2) BnBr, 0.5 h @ -78, then
0.5 h @ 0° C.

The procedure of Example 43 was conducted with the exception that the starting material included the presence of two additional methoxy groups (instead of only one additional methoxy group). After addition of BuLi, a "white suspension" was obtained. However, the alkylated product was not able to be isolated.

Example 45

Exchange

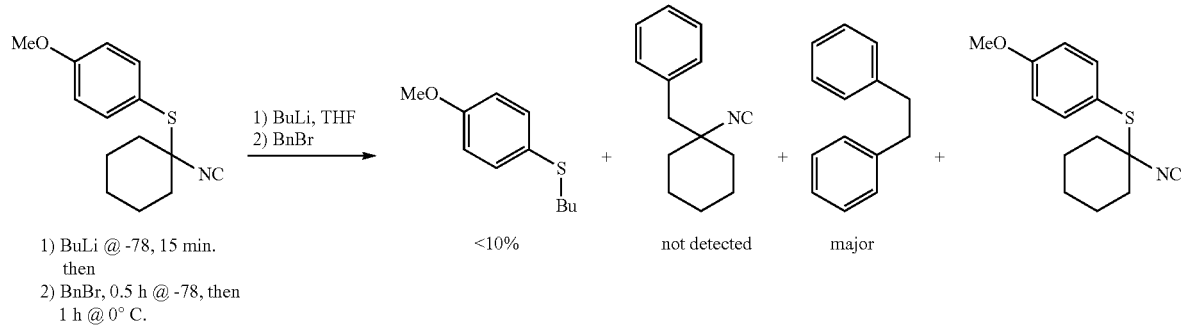

1) BuLi @ -78, 15 min.
then
2) BnBr, 0.5 h @ -78, then
1 h @ 0° C.

The exchange was poor and most of the material was bibenzyl, which indicated that the BuLi was still at the reaction flask and benzyl bromide (metalated once) was in the reaction medium. Metalated benzyl and benzyl bromide coupled/condensed to yield bibenzyl. Based on the results, it was contemplated that the 2-OMe function was effective to direct the organometallic reagent by chelation to promote the formation of the sulfate.

Example 46

Exchange

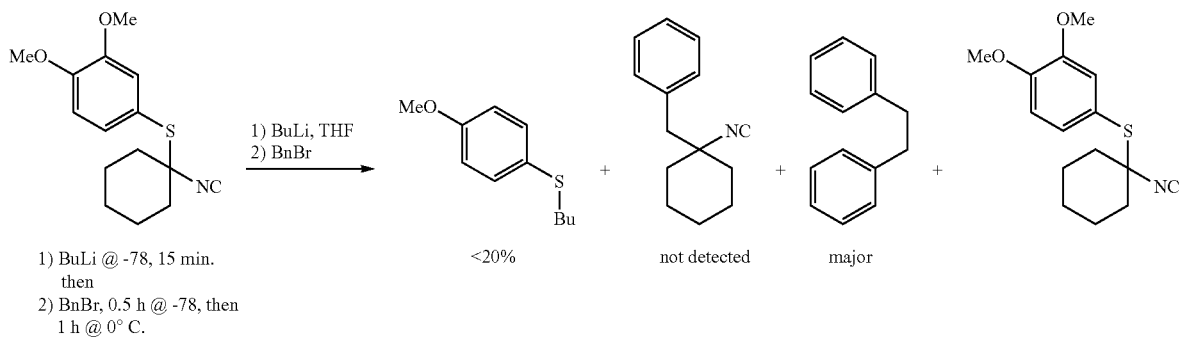

1) BuLi @ -78, 15 min.
then
2) BnBr, 0.5 h @ -78, then
1 h @ 0° C.

The exchange was poor. The main product was bibenzyl which was formed by metalation of benzyl bromide and self condensation. The results indicated that the 2-OMe function was effective to direct the organometallic reagent by chelation to promote the formation of the sulfidate.

Example 47
Exchange

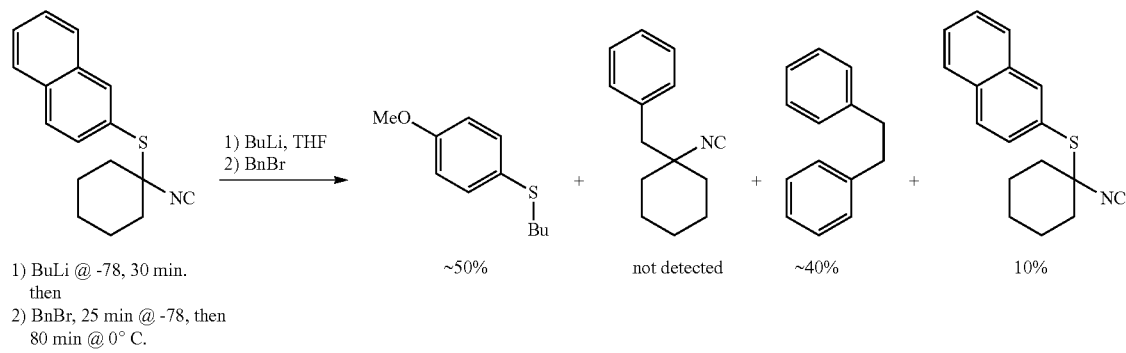

1) BuLi @ -78, 30 min.
   then
2) BnBr, 25 min @ -78, then
   80 min @ 0° C.

Exchange took place, but the isonitrile was not alkylated. The results appeared to demonstrate that the presence of a methoxy group at position 2 or 4 slowed down the exchange. However, the chelation effect boosted the exchange.

Example 48
Exchange

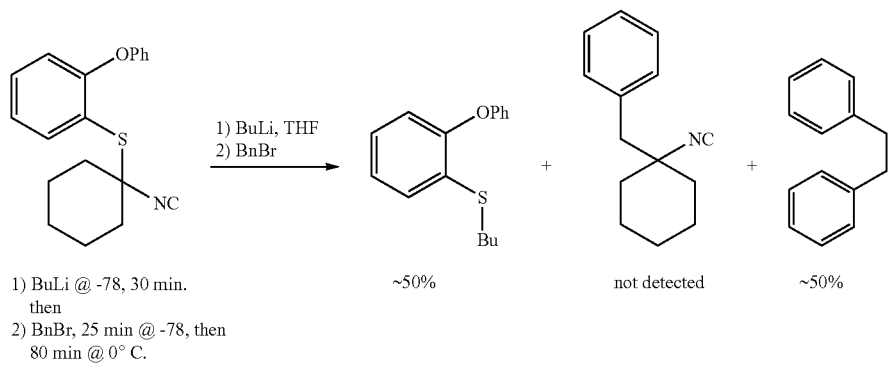

1) BuLi @ -78, 30 min.
   then
2) BnBr, 25 min @ -78, then
   80 min @ 0° C.

The exchange was promoted only partially and it was believed due to the phenyl not providing good coordination of the organometallic reagent toward the formation of the sulfidate. There was no alkylation product since the sulfidate was not stable with the presence of the phenyl as substituent at the oxygen.

Example 49
Exchange

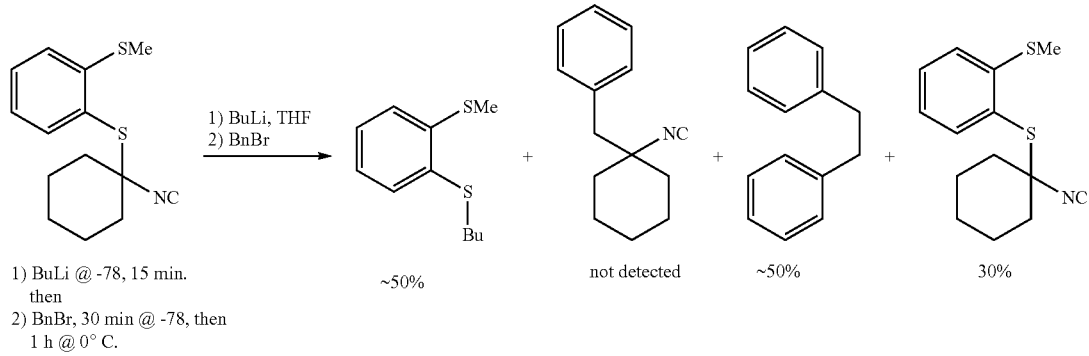

1) BuLi @ -78, 15 min.
   then
2) BnBr, 30 min @ -78, then
   1 h @ 0° C.

Bibenzyl was obtained as one of the major components together with the thioether and SM. It was believed that the results were indicative of sulfur partially promoting the exchange, but not providing stability to the sulfidate. There is no alkylated product.

Example 50

Exchange

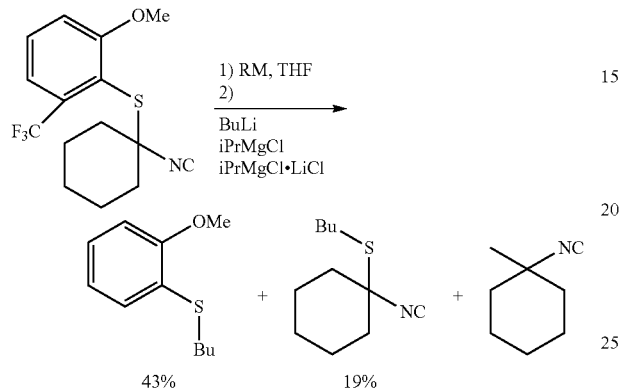

For reaction with BuLi: Exchange was complete, but there was an additional dd at ~2.5 ppm.

For reaction with iPrMgCl: The exchange took place, but it was shown that the cleavage of Ar—S occurred. There was a dd at 2.5 which correlated well with the isocyanocyclohexylbutyl thioether. Without intending to be bound by any particular theory, it was believed this may have resulted from the capability of the trifluoromethyl to retain "charge" or make a "benzyne" byproduct.

For reactions with iPrMgClLiCl): There was no exchange after –78 and 70 min at 0° C. After 24 h there was more than one product. The exchange was not complete after 30 min @ 0° C. The SM was consumed after 24 h, but there was no selectivity.

We claim:

1. An isonitrile compound of a structure of Formula I:

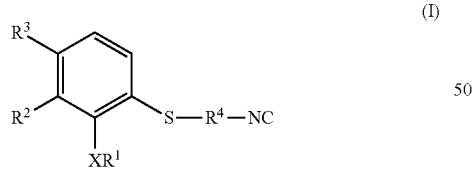

wherein, X is selected from oxygen and sulfur, $R^1$ is selected from alkyl and aryl, $R^2$ is selected from hydrogen and $XR^1$, $R^3$ is selected from hydrogen and $XR^1$, and $R^4$ is selected from alkyl and an aromatic or non-aromatic, cyclic or polycyclic structure, or wherein, X is selected from oxygen and sulfur, $R^1$ is selected from alkyl and aryl, $R^2$ and $R^3$ form a benzo ring, and $R^4$ is selected from alkyl and an aromatic or non-aromatic, cyclic or polycyclic structure.

2. The compound of claim 1, wherein $R^4$ is selected from alkyl and a cyclic six-membered ring.

3. The compound of claim 1, wherein $R^1$ is selected from $C_1$-$C_6$ alkyl and aryl.

4. The compound of claim 1, wherein $R^1$ is selected from $C_1$-$C_4$ alkyl and aryl.

5. The compound of claim 1, wherein said compound has a structure of Formula II:

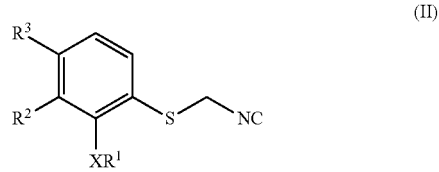

wherein X, $R^1$, $R^2$, and $R^3$ are as defined for Formula I.

6. The compound of claim 1, wherein said compound has a structure of Formula III:

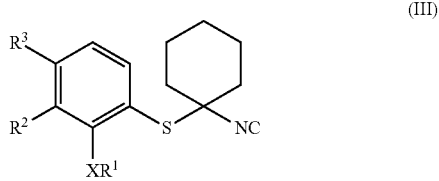

wherein X, $R^1$, $R^2$, and $R^3$ are as defined for Formula I.

7. An isonitrile compound of a structure of Formula IV:

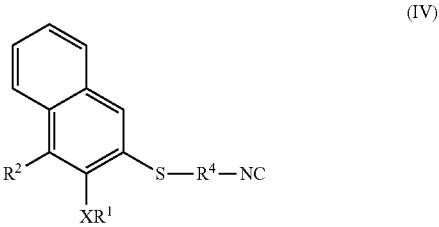

wherein X is selected from oxygen and sulfur, $R^1$ is selected from alkyl and aryl, $R^2$ is selected from hydrogen and $XR^1$, and $R^4$ is selected from alkyl and an aromatic or non-aromatic, cyclic or polycyclic structure.

8. A method of preparing an isonitrile comprising:

reacting a compound of a structure of Formula III:

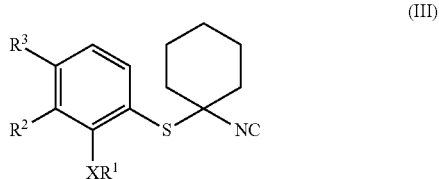

wherein, X is selected from oxygen, sulfur and nitrogen, $R^1$ is selected from alkyl and aryl, $R^2$ is selected from hydrogen and $XR^1$, $R^3$ is selected from hydrogen and $XR^1$, with an electrophile in an exchange reaction to form compounds represented by general structures of Formulas V or VI:

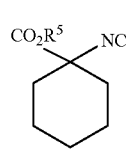
(V)

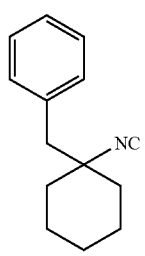
(VI)

wherein, $R^5$ is $C_1$-$C_4$ alkyl.

9. The method of claim 8, wherein the electrophile is selected from the group consisting of diphenyl disulfide, methyl iodide, propyl bromide, propylene oxide, cyclohexanone, propyl iodide, cyclohexenone, and mixtures thereof.

10. The method of claim 8, wherein $R^1$ is selected from $C_1$-$C_6$ alkyl and aryl.

11. The method of claim 8, wherein $R^1$ is selected from $C_1$-$C_4$ alkyl and aryl.

* * * * *